United States Patent [19]
Cheng et al.

[11] Patent Number: 6,137,032
[45] Date of Patent: Oct. 24, 2000

[54] XYLANASE OBTAINED FROM AN ANAEROBIC FUNGUS

[75] Inventors: Kuo-Joan Cheng, Richmond; Leonard Brent Selinger, Lethbridge; Jin-Hao Liu, Calgary, all of Canada; Youji Hu, Gulph Mills, Pa.; Cecil Wallace Forsberg, Guelph, Canada; Maurice Martin Moloney, Calgary, Canada

[73] Assignee: Her Majesty the Queen in right of Canada, as represented by the Department of Agriculture and Agri-Food Canada, Lethbridge, Canada

[21] Appl. No.: 09/390,200

[22] Filed: Sep. 7, 1999

Related U.S. Application Data

[62] Division of application No. 08/749,391, Nov. 13, 1996, Pat. No. 5,948,667.

[51] Int. Cl.$^7$ ..................................................... C12N 5/04
[52] U.S. Cl. ......................... 800/288; 435/200; 435/419; 800/278; 800/306
[58] Field of Search .................................... 435/419, 200; 800/278, 288, 306

[56] References Cited

FOREIGN PATENT DOCUMENTS

93/25693   12/1993   WIPO .

OTHER PUBLICATIONS

Ausubel. F.A. Brent, R. Kingston, R.E., Moore. D.D., Sneidman, J.G. Smith, J.A. and Struhl. K. (eds.) 1990. Current Protocols in Molecular Biology. Green Publishing and Wiley–Interscience, New York.

Blely, P., Mlslovicova, D. and Toman, R. 1988. Remazeol Brilliant Blues–Xylan: A Soluble Chromogenic Substrate for Xylanses. Methods in Enzymology vol. 160:536–542.

Jurgen Brosius, Mary Erfle and Storella, John 1985. Spacing of the –10 and –35 Regions in the *tac* Promoter, J. Biol. Chem. 260:3539–3541.

Chesson, A., Forsberg, C.W. and Grenet, E. 1995. Improving the Digestion of Plant Cell Walls and Fibrous Feeds. In: Journet, M., Grenet, E., Farce, M–H, Theriez, M., Demarquilly, C. (eds). Recent Developments in the Nutrition of Herbivores. Proceedings of the IVth International Symposium on the Nutrition on Herbivores. INRA Editions, Paris 249–277pp.

Ellis, S.B., Brust, P.F., Koutz, P.J., Waters, A.F., Harpold, M.M. and Gingeras, T.R. 1985. Isolation of Alcohol Oxidase and Two Other Methanol Regulated Genes from the Yeast *Pichia pastoris*. Mol. Cell. Biol. 5:1111–1121.

Gelvin, Stanton B., Schliperoort, R.A. and Verma, D.P.S. (eds.) 1993. Plant Molecular Biology Manual. Kluwer Academic Publishers, Boston, MA.

Hodgson, John 1994. The Changing Bulk Biocatalyst Market. Bio/Technology vol. 12:789–790.

Lowe, Susan E., Theodorou, Michael K., Trinci. Anthony P.J., and Hespell, Robert B. 1985. Growth of Anaorobia Rumon Fungi on Defined and Semi–Defined Media Lacking Rumen Fluid. J. Gen. Microbiol. 131:2225–2229.

McBride, Kevin E. and Summerfeld, Kristin R. 1990. Improved Binary Vectors for *Agrobacterium*–mediated Plant Transformation. Plant Mol. Biol. 15:269–276.

McNeil, Michael, Darvill, Alan G., Fry, Stephen C. and Albersheim, Peter 1984. Structure and Function of the Primary Cell Walls of Plants. Ann Rev Biochem. 53:625–663.

Sambrook, J., Fritsch, E.F. and Maniatis, T. 1989. Molecular Cloning. A Laboratory Manual. 2nd edn. Cold Spring Harbor Laboratory Press. Cold Spring Harbor, NY.

Somogyi, Michael J. 1952. Notes on Sugar Determination. J. Biol. Chem. 195:19–23.

Tamblyn Lee, J.M., Hu, Y., Zhu, H., Cheng, K.–J., Krell, P.J. and Forsberg, C.W. 1993. Cloning of Xylanase Gene from the Ruminal Fungus *Neocallimastix patriciarum 27* and its Expression in *Escherichia coli*. Can J. Microbiol. 39:134–139.

Teather, Ronald M. and Wood, Peter J. 1982 Use of Congo Red–Polysaccharide Interactions in Enumeration and Characterization of Cellulolytic Bacteria from the Bovine Rumen. Appl. Environ. Microbiol. 43:777–780.

van Rooljen. Gijs J.H. and Moloney, M.M. 1995. Plant Seed Oil–Bodies as Carriers for Foreign Proteins. Bio/Technology 13:72–77.

van Rooljen, Gijs J.H. and Moloney, M.M. 1995. Structural Requirements of Oleosin Domains for Subcellular Targeting to the Oil Body, Plant Physiol. 109:1353–1361.

Wong, Sui–Lam. 1989. Development of an inducible and Enhancible Expression and Secretion System in *Bacillus subtilis*. Gene. 83:215–223.

Dayhoff, M.O., Schwartz, R.M. and Orcutt, B.C. 1978. A Module of Evoluntionary Change in Proteins. In: Atlas of Protein Sequence and Structure. vol. 5, Supplement 3, 22:345–352.

(List continued on next page.)

*Primary Examiner*—Charles L. Patterson, Jr.
*Attorney, Agent, or Firm*—Greenlee, Winner and Sullivan, P.C.

[57]   ABSTRACT

A xylanase gene, denoted xynC, encoding a novel xylanase (XynC) obtained from the anaerobic fungus *Neocallimastix patriciarum* is provided. The DNA sequence of the xynC gene is also provided. Transformation of microbial and plant hosts with the xynC gene is described. The xynC gene may be used to design probes for use in hybridization experiments to isolate xylanase genes from other anaerobic fungi. The xynC gene has been used to construct an oleosin-xynC expression construct encoding an oleosin-xylanase fusion protein which retains xylanase activity. Transgenic *Brassica napus* (canola), transformed with the oleosin-xynC expression construct, expresses the oleosin-xylanase fusion protein which is immobilized in the oil-body membrane of the *B. napus* seeds. Canola meal, the protein-rich residue left after canola oil is extracted from canola plants, when derived from the transgenic *B. napus* of the present invention, retains substantial xylanase activity, making it an ideal animal feed supplement.

18 Claims, 6 Drawing Sheets

OTHER PUBLICATIONS

Gilbert, H.J. et al., "Homologous catalytic domains in a rumen fungal xylanase—Evidence for gene duplication and prokaryotic origin," (1992) *Mol. Microbiol.* 6:2065–2072.

Black, G.W. et al., "Xylanase B from *Neocallimastix patriciarum* contains a non–catalytic 455–residue linker sequence comprised of 57 repeats of an octapeptide," (1994) *Biochem J.* 299:381–387.

Fanutti, C. et al., "The conserved noncatalytic 40–residue sequence in cellulases and hemicellulases from anaerobic fungi functions as a protein docking domain," (1995) *J. Biol. Chem.* 49:29314–29322.

Selinger et al. poster of a presentation entitled "Characterization of a xylanase gene from *Neocallimastix patriciarum*" given at the 23$^{rd}$ Biennial Conference on Rumen Function, Nov. 14, 1995, Chicago, Illinois.

Selinger et al. Abstract of "Characterization of a xylanase gene from *Neocallimastix patriciarum*" (1995) 23$^{rd}$ Conf. Rumen Function.

Xue, G.P. et al., "Modification of a xylanase cDNA isolated from an anaerobic fungus *Neocallimastix patriciarum* for high–level expression in *Escherichia coli*," (1995) *J. Biotechnol.* 38:269–277.

FIG. 3A

```
  1 ATATTATAATAATTGTTCAAAAAAAATAATAAAAAGTAATAATAAAAAAATTTTTTTTTTT   60
 61 GGGAAAATTGAGTATAAAATAGTTTTTGGTTACCTTTTTTTGGTTTTTCCTTTATTCTTTA  120
121 TAAAGTTAATTGTTTAATAATTATTGGTGAAAATATTTAAAAGTTGTATATATATTTTAA  180
181 TATTTATTGGAATTATTTACTTTACTTGTGGAAACAAATATTAATAGTGTATAATATAT  240
241 TATTAGAAAAAGAAAAAAAATTATTACAATTAATTACTATAAATAAAATAGTTAAAA  300
301 ATGAAATTTTACAAATTATTCCTGTATTATCTTTAACTTCAACTACTCTTGCTCAA  360
      M  K  F  L  Q  I  I  P  V  L  S  L  T  S  T  T  L  A  Q
                                    10                      20
361 AGTTTCTGTAGTTCAGCTTCTCACTCTGGACAAAGTGTAAAGGAAACCGGCAACAAGGTT  420
     S  F  C  S  S  A  S  H  S  G  Q  S  V  K  E  T  G  N  K  V
                     30                      40
421 GGAACTATTGGTGGTGTTGGTTACGAATATGGGCTGATAGTGGTAATAACAGTGCTACT  480
     G  T  I  G  G  V  G  Y  E  L  W  A  D  S  G  N  N  S  A  T
             50                      60
481 TTCTATTCTGATGGTTCCTTCTCAAATGCTGGGGATTACTTATGTCGT  540
     F  Y  S  D  G  S  F  S  C  F  Q  N  A  G  D  Y  L  C  R
     70                      80
541 AGTGGGTCTCTTCTTTCGATAGTACTAAGACAAAATATTCCAAATGTTATTCCTATGAAGGCTGAT  600
     S  G  L  L  F  D  S  T  K  T  K  Y  F  P  S  Q  W  L  F  L  C  W  M  K  A  D
                     90                     100
601 TTCAAACTGTCAAACTTGTCGATAATGTTGGTTATTCCGATAATGTTGGTTCCTGATAATGGT  660
     F  K  L  V  K  T  Y  F  G  I  H  V  D  N  W  L  F  L  C  W  L  R
             110                     120
661 TGGACTAGAAGTCCACTTGTCAAGAAGCATGGTTCTTTCACTATTGATGGCTAATAC  720
     W  T  R  S  P  L  V  K  K  H  G  S  F  T  I  D  G  A  Q  Y
     130                     140                     150                     160
721 CCAGGTGATTGGTGTTGGTTAACAAGAGCATGGTTCTTTCACTATTGATGGTGCTCAATAC  780
     P  G  D  W  V  G  N  K  K  H  G  S  F  T  I  D  G  A  Q  Y
                     150                     160
781 ACTGTTTATGAAAACACTCGTACTGGTAATGATGGTAATACCACCTTCAAACAA  840
     T  V  Y  E  N  T  R  T  G  P  S  I  D  G  N  T  F  K  Q
                     170                     180
```

FIG. 3B

```
841  TACTTTAGTATTCGTCAACAAGCTCGTGATTGTGGTACCATTGATATTTCTGCTCACTTT  900
      Y  F  S  I  R  Q  Q  A  R  D  C  G  T  I  D  I  S  A  H  F
                    HindIII                                          200
901  GATCAATGGGAAAAGCTTGGTATGACTATGGGTAAATTACATGAAGCCAAGGTTTTAGGT  960
      D  Q  W  E  K  L  G  M  T  M  G  K  L  H  E  A  K  V  L  G
                         190                            210           220
961  GAAGCCGGTAACGGTGGTGTCAGTGGTACTGCTGATTTCCCATACGCAAAGGTT      1020
      E  A  G  N  G  G  V  S  G  T  A  D  F  P  Y  A  K  V
                    210           230                      240
1021 TACATTGGTGATGGAAATGGTGGTGCTTCTCCAGCTCCAGCTGGTGGCGCTCCAGCA    1080
      Y  I  G  D  G  N  G  G  A  S  P  A  P  A  G  G  A  P  A
            PvuII                                              260
1081 GGCGGCGCTCCAGCCGGTCAACGGACCAAGGACCAACAAGGTCAACAACCACCACAA    1140
      G  G  A  P  A  G  Q  R  T  K  D  Q  Q  G  Q  Q  P  P  Q
            250                              270                280
1141 GGTCAACAAGGTCAACAAGGACCAACAAGGACCAACAAGGTCAACAACCACCACCA     1200
      G  Q  Q  G  Q  Q  G  P  T  Q  Q  G  P  T  Q  Q  P  P  P
                290                        310                    320
1201 CAACCACCAAGGTCAACGATCAACAACAAGGACCAACAAGGACCAACAAGGACCAAGGAGGT  1260
      Q  P  P  Q  Q  R  S  T  T  R  T  N  K  D  Q  Q  G  P  Q  G
                       310                                        320
1261 CAAGGTAACGATCAACAACAAGGACCAACAAGGACCAACAAGGACCAACAAGGACCAAGGAGGT  1320
      Q  G  N  D  Q  Q  Q  G  P  Q  G  P  Q  G  P  Q  G  P  Q  G
                              330                                    340
1321 AACCCAGGTGGTAGTCCATGGGAACTGGAACCAAGGTAGTCCATGGGTTGGTAAT      1380
      N  P  G  G  S  P  W  N  W  N  Q  G  S  P  W  G  G  N
                      350                           350              360
1381 CAAGGTGGTAGTCCATGGGAAATCCATGGGGAGGAAACCAAGGT               1440
      Q  G  G  S  P  W  G  N  P  W  G  G  N  Q  G
                    370                              380
1441 GGTAGCCCATGGGGTCAAGTCCAGTCCAAGGTAACCAAGGTAACCAAGGCGGT        1500
      G  S  P  W  G  Q  V  Q  S  Q  G  N  Q  G  N  Q  G  G
                   390                              400
```

FIG. 3C

```
1501 AATCCATGGGGAGGAAACCAAGGTGGTAGCCCATGGGGTGGTAACCAAGTGGTAATCCA   1560
      N  P  W  G  G  N  Q  G  S  P  W  G  G  N  Q  G  N  P
                                410                         420
1561 TGGGGTGGTAATCAATGGGGTGCTCCACAAAATGCTGCTCCACAAAGCGCTGCTGCT     1620
      W  G  G  N  Q  W  G  A  P  Q  N  A  A  P  Q  S  A  A
                                430                         440
1621 CCACAAAACGCTTCTGATGGTGGTAACTGTGCTTCTCTTTGGGGTCAATGCGGTGGACAA  1680
      P  Q  N  A  S  D  G  G  N  C  A  S  L  W  G  Q  C  G  Q
                                450                         460
1681 GGTTATAATGGTCCATCTTGCTGTTCCGAAGGTTCCTGTAAGCCAATTAACGAATACTTC  1740
      G  Y  N  G  P  S  C  C  S  E  G  S  C  K  P  I  N  E  Y  F
                                470                         480
1741 CACCAATGTCAAAAATAAGATTAGAAATCATTATCAACCCATATTTATTTGTGTAGAT   1800
      H  Q  C  Q  K  *
1801 TAAAATAATAATAATCATTATCAACAAAAAAAAATTTTTTTATTTTTTTTCTCCTCAATT 1860
1861 AATAAATCATTATCAACAAAATAATAGATCATTAAATATTTCATTTTTATTTTTTTTAA  1920
1921 TTAATACGTAAATGTAAATTAAACAATTTAAAACAATTTATTTAATTTAATATTTATAAA 1980
1981 AGATACTATTTTAATAATAAATTTATAAAAATATATATAAAAATATAAAAAAAAAAAAA  2040
2041 AAAAAATATTAATGAAAGT                                          2058
```

XYLANASE OBTAINED FROM AN ANAEROBIC FUNGUS

The present application is a Divisional Application of U.S. patent application Ser. No. 08/749,391, filed Nov. 13, 1996, now U.S. Pat. No. 5,948,667.

FIELD OF THE INVENTION

The present invention relates to the field of molecular biology. In particular, the invention relates to genes encoding xylanases obtained from strains of the anaerobic fungus *Neocallimastix patriciarum*.

BACKGROUND OF THE INVENTION

Endo-xylanases are enzymes that randomly cleave the β(1–4) linkages between xylose residues making up the backbone of xylans, a prevalent form of hemicellulose found predominantly in plant primary and secondary cell walls. If this complex plant cell wall polysaccharide is hydrolyzed with xylanases, it can be exploited as a rich source of carbon and energy for the production of livestock and microorganisms. Enzymatic disruption of plant cell walls also increases the efficiency of a number of industrial processes such as juice extraction, retting of flax fibers and pulp production. As discussed in greater detail herein, it will be appreciated that plant cell walls are highly variable structures containing several forms of hemicellulose. Thus, the need exists to identify and produce novel xylanases that are efficient at degrading this complex polysaccharide.

The plant cell wall is a highly variable, complex and resilient structure encasing essentially every cell of higher plants. It represents a rich store of carbon and energy for herbivores as well as an important renewable resource utilized by the pulp and paper, lumber, food, and pharmaceutical industries. The plant cell wall consists largely of polysaccharides and contains lesser amounts of lignin (phenolic esters) and protein. The primary polysaccharide components of plant cell walls are cellulose (a hydrogen-bonded β(1–4)-linked D-glucan), hemicellulose, and pectin (McNeil et al., 1984). Fibrils of cellulose embedded in a matrix of pectin, hemicellulose (comprising various β-xylan polymers), phenolic esters and protein produce a protective structure resistant to dehydration and penetration by phytopathogens through mechanical and enzymatic mechanisms.

Hemicellulose, the second most prevalent polysaccharide in many plant cell walls is composed mainly of xyloglucan or xylan polymers. Xyloglucans consist of a backbone of β-4-linked-D-glucosyl residues substituted with α-linked D-xylosyl side chains, some of which are extended by fucose, galactose or arabinose residues (McNeil et al., 1984). Xylans have a backbone structure of β(1–4)-linked xylose residues. The structure of xylan is complicated by the attachment of various side chains (e.g., acetic acid, arabinose, coumaric acid, ferulic acid, glucuronic acid, 4-O-methylglucuronic acid) to the xylose residues (McNeil et al., 1984). The strands of hemicellulose are hydrogen bonded to cellulose fibrils to form a strong interconnected lattice.

Cell wall composition varies with plant species, variety, tissue type, growth conditions, and age. Differences in cell wall composition have been reported between dicotyledonous and monocotyledonous plants (Chesson et al., 1995). The primary cell walls of all dicots and many monocots contain greater amounts of xyloglucan than arabinoxylan. In contrast, plants belonging to the family Gramineae (e.g., grasses and cereal) have primary walls in which only cellulose is more abundant than arabinoxylan. Higher pectin concentrations are found in the exterior wall or middle lamellae than in the primary or secondary cells walls. Finally, as cells age, cell walls may become more lignified and resistant to microbial attack.

The complexity of the plant cell wall is related not only to compositional variation but also to the high degree of interaction between constituent cellulose, hemicellulose and pectin molecules. Dual intermeshing networks of polysaccharides, comprising cellulose fibrils crosslinked with hemicellulose and pectic polysaccharides linked by calcium bridges, not only produce a resilient primary cell wall but are of direct relevance to enzymatic degradation (Chesson et al., 1995).

Digestion of the plant cell wall is further complicated by the structure of polysaccharides. Cellulose is a simple unsubstituted polymer of β(1–4)-linked glucose and requires an endoglucanase and cellobiose for complete degradation. In comparison, highly substituted arabinoxylan requires up to seven different enzymes for complete degradation. An endo-xylanase randomly cleaves the xylan backbone into xylooligosaccharides which are subsequently degraded to xylose by a xylosidase. Substituents are cleaved from the xylan backbone with arabinofuranidase, acetylxylan esterase and α-glucuronidase. Ferulic and p-coumaric acid crosslinks are degraded by feruloyl and p-coumaryl esterases. If complete degradation of the arabinoxylan is not required, fewer enzymes may be needed. Liquefaction of arabinoxylan requires only the shortening of the xylan polymers. Consequently, this objective may be achieved by the production of xylooligosaccharides through the action of a single endo-xylanase. The choice of enzymes is dependent upon the substrate to be degraded.

The known applications of xylanases are numerous. For instance, the treatment of forages with xylanases (along with cellulases) to increase the rate of acid production, thus ensuring better quality silage and improvement in the subsequent rate of plant cell wall digestion by ruminants has been described. Xylanases can be used to treat rye, and other cereals with a high arabinoxylan content to improve the digestibility of cereal by poultry and swine. Xylanases can be used in bioconversion involving the hydrolysis of xylan to xylooligosaccharides and xylose which may serve as growth substrates for microorganisms. This could involve simultaneous saccharification and fermentation. Xylanases can be used in biopulping to treat cellulose pulps to remove xylan impurities or to produce pulps with different characteristics. In some cases they can be applied to reduce the amount of chlorine needed to bleach the pulp and reduce the energy needed for refining pulp. Further, xylanases are useful in the retting of flax fibers, the clarification of fruit juices, the preparation of dextrans for use as food thickeners and the production of fluids and juices from plant materials.

Some characteristics of an endo-xylanase from *N. patriciarum* strain 27 (from the Agriculture and Agri-Food Canada Lethbridge culture collection) have been reported previously (Tamblyn Lee et al., 1993). Tamblyn Lee et al. described the isolation of a 6.5 kb EcoRI fragment containing a gene encoding an endo-xylanase. The *N. patriciarum* strain 27 was not disclosed or made publicly available. The location of the xylanase gene was narrowed down to a 3.6-kb EcoRI SalI fragment. Expression of the endo-xylanase gene in *E. coli* produced at least three proteins (51, 58 and 68 kDa) having xylanase activity. This study did not fully characterize the *N. patriciarum* strain 27 endo-xylanase gene. No attempt was made to determine the nucleotide sequence of the gene. Nucleotide sequence data is required to create an efficient fusion construct between the endo-xylanase gene and the sequences of a heterologous expression system. Without this information, the large DNA fragments of Tamblyn Lee et al. would not be useful for the construction of a functional gene fusion. This effort would be hampered by a lack of detailed information about the structure of the gene and the location of useful restriction sites. The large DNA fragments identified by Tamblyn Lee et al. are not useful for commercial enzyme production. Specifically, if these large DNA fragments were cloned into efficient expression systems, translation of the resulting transcripts transcribed from a strong heterologous promoter would not be possible as transcription would be terminated at one of the multiple stop codons found in AT rich sequences upstream from the endo-xylanase gene. Further characterization, isolation and nucleotide sequencing of the *N. patriciarum* strain 27 endo-xylanase gene would be required if it were to be of commercial importance.

In light of the many industrial applications for xylanases, the need for new xylanases is apparent. Accordingly, it is of great importance to obtain genes encoding xylan-degrading enzymes from novel sources which may be brought to expression in other, high-producing microbial or eukaryotic expression systems.

SUMMARY OF THE INVENTION

In accordance with the present invention, DNA sequences encoding novel and useful xylanases derived from anaerobic fungi are provided. As used herein and in the claims, the term "xylanase" means an enzyme having xylan degrading activity.

A xylanase gene (xynC) from *Neocallimastix patriciarum* strain 27 from the Agriculture and Agri-Food Canada culture collection at Lethbridge, Alberta, Canada has been cloned and sequenced, and the nucleotide sequence of a DNA fragment including xylanase encoding region (CDS) of the xynC gene is provided in SEQ ID NO. 1. *Escherichia coli* strain DH5α (pNspX-04), carrying the xynC gene was deposited Nov. 8, 1996 with the American Type Culture Collection, 12301 Parklawn Drive, Rockville, Md., 20852-1776, as ATCC 98249.

The invention extends to DNA sequences which encode xylanases and which are capable of hybridizing under stringent conditions with all or part of the xynC gene sequence. As used herein and in the claims, "capable of hybridizing under stringent conditions" means annealing to a subject nucleotide sequence, or its complementary strand, under standard conditions (i.e., high temperature and/or low salt content) which tend to disfavor annealing of unrelated sequences. As used herein and in the claims, "conditions of low stringency" means hybridization and wash conditions of 40°–50° C., 6×SSC and 0.1% SDS (indicating about 50–80% homology). As used herein and in the claims, "conditions of medium stringency" means hybridization and wash conditions of 50°–65° C., 1×SSC and 0.1% SDS (indicating about 80–95% homology). As used herein and in the claims, "conditions of high stringency" means hybridization and wash conditions of 65°–68° C., 0.1×SSC and 0.1% SDS (indicating about 95–100% homology).

A method for identifying other nucleic acids having xylanase activity is also provided wherein nucleic acid molecules are isolated from an organism and nucleic acid hybridization is performed with the nucleic acid molecules and a labelled probe having a nucleotide sequence that includes all or part of nucleotide sequence SEQ ID NO. 1. By this method, xylanase genes similar to the xynC gene may be identified and isolated from other anaerobic fungi.

The invention extends to purified and isolated xylanases obtained from strains of *Neocallimastix patriciarum*, particularly *Neocallimastix patriciarum* strain 27. A preferred xylanase has the amino acid sequence shown in SEQ ID NO. 2.

The invention extends to expression constructs constituting a DNA having a coding region encoding a xylanase of the present invention operably linked to control sequences capable of directing expression of the xylanase in a suitable host cell. The control sequences may be homologous to or heterologous to the xylanase encoding region. As used herein and in the claims, the term "homologous" DNA refers to DNA originating from the same species as the host cell or control sequences, as the context requires. For example, *Aspergillus niger* may be transformed with DNA from *A. niger* to improve existing properties without introducing properties that did not exist previously in the species. As used herein and in the claims, "heterologous" DNA refers to DNA originating from a different species. For example, the *N. patriciarum* strain 27 xynC may be cloned and expressed in *E. coli*.

The invention further extends to host cells which have been transformed with, and express DNA encoding a xylanase of the present invention, and to methods of producing such transformed host cells. As used herein and in the claims, "host cell" includes animal, plant, yeast, fungal, protozoan and prokaryotic host cells.

The invention further extends to transgenic plants which have been transformed with a DNA encoding a xylanase of the present invention so that the transformed plant is capable of expressing the xylanase and to methods of producing such transformed plants. As used herein and in the claims, "transgenic plant" includes transgenic plants, plant tissues and plant cells. In a preferred embodiment, the transformed plant is of the species *Brassica napus* (canola).

The present invention also extends to oleosin-xylanase fusion proteins, DNA sequences encoding oleosin-xylanase fusion proteins, and transgenic plants, preferably *B. napus*, which have been transformed to express such oleosin-xylanase fusion proteins. Surprisingly, these oleosin-fusion proteins have been discovered to retain xylanase activity. When *B. napus* is transformed with a DNA sequence of the present invention encoding an oleosin-fusion protein, the oleosin-fusion protein may immobilized in the membrane surrounding the oil-bodies found in the *B. napus* seeds. The canola oil is extracted from the seeds by, for instance, crushing, leaving a solid fraction and an oil fraction. Disruption of oil-body membranes in the oil fraction leaves tha oil-body membranes forming a gum which can be separated from the oil. The gum contains the oleosin-xylanase fusion protein. The gum is then added to the solid during the production of canola meal. Canola meal is a low-cost animal feed supplement which is high in protein. Canola meal made from transgenic *B. napus* transformed with a DNA sequence encoding an oleosin-xylanase fusion protein therefore also provides an excellent source of supplemental xylanase for the animal.

Xylanases of the present invention are useful in a wide variety of applications involving the degradation of xylan. Accordingly, the invention extends to feed supplements containing a xylanase of the present invention. Such feed supplements may also contain other enzymes, such as proteases, cellulases, phytases and acid phosphatases. The xylanase may be added directly to an untreated, pelletized, or otherwise processed feedstuff, or it may be provided separately from the feedstuff in, for instance, a mineral block, a pill, a gel formulation, a liquid formulation, or in drinking water.

DETAILED DESCRIPTION OF THE INVENTION

Figure 1:
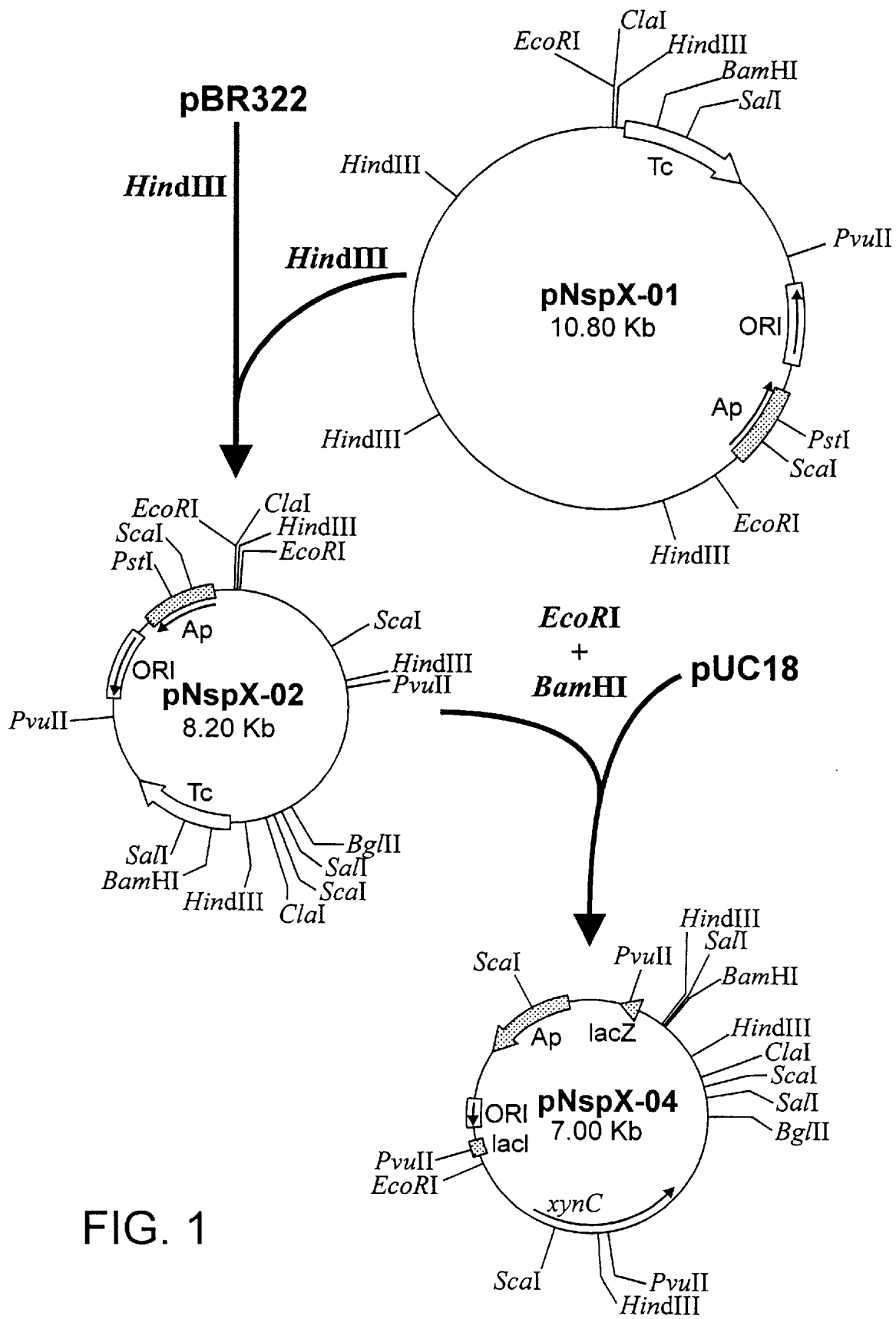
FIG. 1 depicts a construction pathway of plasmid constructs carrying an endo-xylanase gene cloned from *N. patriciarum* 27.

The present invention provides purified and isolated DNA sequences of anaerobic fungal origin, which encode xylanases and genetic variants thereof. The DNA sequence preferably includes the xylanase-encoding region (CDS, protein coding sequence). Genetic variants include hybrid DNA sequences containing the xylanase CDS fused to regulatory regions such as promoter, leader peptide and terminator signals, originating from homologous or heterologous sources. Genetic variants also include DNA sequences encoding mutant xylanase proteins and degenerate DNA sequences wherein the xylan-degrading activity of the enzyme is retained. The present invention provides the starting material for the construction of "second generation" xylanases, i.e., mutant xylanases with properties that differ from those of the enzymes isolated herein, or DNA sequences (encoding the xylanase CDS) altered to reflect the degeneracy of the genetic code or cross-species variation. Genes can be readily mutated by procedures known in the art (e.g., chemical, site directed, random polymerase chain reaction mutagenesis) thereby creating gene products with altered properties (e.g., temperature or pH optima, specific activity or substrate specificity). The xylanase gene of the present invention can be used also in heterologous hybridization and polymerase chain reaction experiments, directed to isolation of xylanase-encoding genes from other natural sources.

Screening organisms for endo-xylanase activity can be accomplished by a number of assays methods not critical to the present invention. These include visual assays such as the incorporation of xylan (e.g., oat spelt xylan, rye arabinoxylan) or chromogenic substrates (e.g., remazol brilliant blue xylan or RBB-xylan) into agar media. Hydrolysis of the xylan is indicated by the presence of zones of clearing around isolates with endo-xylanase activity. Staining of the medium with Congo red (Teather and Wood, 1982) allows visualization of the hydrolytic activity on solid medium containing non-chromogenic substrates such as oat spelt xylan.

Once a xylanase of interest has been identified, the DNA sequence encoding such a xylanase is cloned from the organism which naturally produces the xylanase by a variety of methods. Gene libraries (genomic DNA and/or cDNA) are constructed by standard methods (Ausubel et al., 1990; Sambrook et al., 1989) and screened for the desired gene. In the case of eukaryotic organisms and inducible xylanase expression, it may be advantageous to construct cDNA libraries with mRNA isolated from the organism, which naturally produces the xylanase, following cultivation in an inducing medium (e.g., a medium containing straw or xylan as the sole carbon source). Clones carrying the desired xylanase gene can be isolated by screening the library with enzyme activity assays (Teather and Woods, 1982), heterologous probes, or results generated during purification of the gene product, such as N-terminal and internal amino acid sequence data and antibodies.

Using Congo red detection, a *Neocallimastix patriciarum* strain 27 genomic DNA library was screened for lambda clones possessing xylanase activity (Tamblyn Lee et al., 1993). A xylanase positive clone carrying a 6.5-kb EcoRI insert was identified and confirmed by Southern blot hybridization to have originated from *N. patriciarum* strain 27.

Plasmid DNA extracted from the newly isolated clone and introduced into *E. coli* cells by transformation produced ampicillin resistant, xylanase positive colonies. Zymogram analysis of cell extracts from *E. coli* DH5α cells carrying a 3.5-kb EcoRI SalI DNA fragment isolated from the original 6.5-kb EcoRI fragment showed active bands of 68, 58, and 51 kDa. The gene (xynC), encoding the observed xylanase activity in recombinant *E. coli* clones, was identified by deletion and nucleotide sequence analysis. The nucleotide sequence and deduced amino acid sequence are shown in FIGS. 3A–3C, and further illustrate that the cloned sequence encoded a xylanase.

It is known in the biological arts that certain amino acid substitutions can be made in protein sequences without affecting the function of the protein. Generally, conservative amino acid substitutions are tolerated without affecting protein function. Similar amino acids can be those that are similar in size and/or charge properties, for example, aspartate and glutamate and isoleucine and valine are both pairs of similar amino acids. Similarity between amino acid pairs has been assessed in the art in a number of ways. For example, Dayhoff et al. (1978) in *Atlas of Protein Sequence and Structure*, Volume 5, Supplement 3, Chapter 22, pages 345–352, which is incorporated by reference herein, provides frequency tables for amino acid substitutions which can be employed as a measure of amino acid similarity. Dayhoff et al.'s frequency tables are based on comparisons of amino acid sequences for proteins having the same function from a variety of evolutionarily different sources.

It is also known that often less than a full length protein has the function of the complete protein, for example, a truncated protein lacking an N-terminal, internal or a C-terminal portion often has the biological and/or enzymatic activity of the complete natural protein. Those of ordinary skill in the art know how to make truncated proteins and proteins with internal deletions. In the present invention, the function of a truncated xylanase protein or an internally deleted xylanase protein can be readily tested using the xylanase assay described hereinbelow and in view of what is generally known in the art.

Substituted and truncated xylanase derivatives which retain substantially the same the enzymatic activity of the xylanase specifically disclosed herein are considered equivalents of the exemplified xylanase and are within the scope of the present invention, particularly where the specific activity of the substituted or truncated xylanase derivative is at least about 10% of the specifically exemplified xylanase. The skilled artisan can readily measure the activity of a truncated or substituted xylanase using the assay procedures taught herein and in view of what is generally known in the art.

This invention includes structurally variant xylanases derived from a xylanase obtained from an anaerobic fungus, particularly those derived from a xylanase specifically disclosed herein, that are substantially functionally equivalent to that xylanase as assayed as described herein in view of what is generally known in the art. Structurally variant, functional equivalents of the xylanases of this invention include those xylanases of an anaerobic fungus having a contiguous amino acid sequence as in the xylanase amino acid sequence disclosed herein (SEQ ID NO. 2), particularly those variant xylanases which have a contiguous amino acid sequence of a xylanase of an anaerobic fungus, where a contiguous sequence is at least about 25 amino acids in length.

As with other genes, it is possible to use the characterized xylanase-coding sequences from anaerobic fungi in a variety of expression systems for commercial protein production. Application of recombinant DNA technology has enabled enzyme manufacturers to increase the volume and efficiency of enzyme production, and to create new products. The original source organism need no longer limit the production of commercial enzymes. Genes encoding superior enzymes can be transferred from organisms such as anaerobic fungi, typically impractical for commercial production, into well characterized industrial microbial production hosts (e.g., Aspergillus, Pichia, Trichoderma, Bacillus spp.). As well, these genes can be transferred to novel plant and animal expression systems.

Industrial strains of microorganisms (e.g., *Aspergillus niger, Aspergillus ficcum, Aspergillus awamori, Aspergillus oryzae, Trichoderma reesei, Mucor miehei, Kluyveromyces lactis, Pichia pastoris, Saccharomyces cerevisiae, Escherichia coli, Bacillus subtilis* or *Bacillus licheniformis*) or plant hosts (e.g., canola, soybean, corn, potato) may be used to produce xylanases. All systems employ a similar approach to gene expression. An expression construct is assembled to include the protein coding sequence of interest and control sequences such as promoters, enhancers and terminators. Other sequences such a signal peptide sequences and selectable markers may be included. To achieve extracellular expression of xylanase, the expression construct of the present invention utilizes a secretory signal peptide sequence. The signal peptide sequence is not included on the expression construct if cytoplasmic expression is desired. Transcriptional terminators are included to ensure efficient transcription. Ancillary sequences enhancing expression or protein purification may also be included in the expression construct. The promoter, enhancer, signal peptide and terminator elements are functional in the host cell and provide for efficient expression and secretion of the xylanase.

The xylanase-coding sequences are obtained from anaerobic fungal sources. Various promoters (transcriptional initiation regulatory region) may be used according to the present invention. The selection of the appropriate promoter is dependent upon the proposed expression host. The promoter may be homologous or heterologous to the cloned protein coding sequence. Examples of heterologous promoters are the *E. coli* tac and trc promoters (Brosius et al., 1985), *Bacillus subtilis* sacB promoter and signal sequence (Wong, 1989), aox1 and aox2 from *Pichia pastoris* (Ellis et al., 1985), and oleosin seed specific promoter from *Brassica napus* (van Rooijen and Moloney, 1995a). Promoter selection is also dependent upon the desired efficiency and level of peptide or protein production. Inducible promoters such tac and aox1 are often employed in order to dramatically increase the level of protein expression. Overexpression of proteins may be harmful to the host cells. Consequently, host cell growth may be limited. The use of inducible promoter systems allows the host cells to be cultivated to acceptable densities prior to induction of gene expression, thereby, facilitating higher yields of product. If the xylanase-coding sequence is to be integrated through a gene replacement (omega insertion) event into a target locus, then promoter selection may also be influenced by the degree of homology to the target locus promoter.

Various signal peptides may be used according to the present invention. A signal peptide sequence which is homologous to the xylanase-coding sequence to be expressed may be used. Alternatively, a signal peptide sequence which has been selected or designed for improved secretion in the expression host may also be used, for example, *B. subtilis* sacB signal peptide for secretion in *B. subtilis*, the *Saccharomyces cerevisiae* α-mating factor or *P. pastoris* acid phosphatase pho1 signal sequences for *P. pastoris* secretion. A signal peptide sequence with a high degree of homology to the target locus may be required if the xylanase-coding sequence is to be integrated through an omega insertion event. The signal peptide sequence may be joined directly through the sequence encoding the signal peptidase cleavage site to the xylanase-coding sequence, or through a short nucleotide bridge consisting of usually fewer than ten codons.

Elements for enhancing expression transcription (promoter activity) and translation have been identified for eukaryotic protein expression systems. For example, the positioning the Cauliflower Mosaic Virus (CaMV) promoter 1000 bp on either side of a heterologous promoter may elevate transcriptional levels by 10 to 400 fold. The expression construct should also include the appropriate translational initiation sequences. Modification of the expression construct to include the Kozak consensus sequence for proper translational initiation may increase the level of translation by 10 fold.

Elements to enhance purification of the protein may also be included in the expression construct. The product of oleosin gene fusions is a hybrid protein containing the oleosin gene joined to the gene product of interest. The fusion protein retains the lipophilic properties of oleosins and is incorporated in the oil body membranes (van Rooijen and Moloney, 1995a). Association with the oil bodies may be exploited to facilitate the purification of the recombinant oleosin fusion proteins (van Rooijen and Moloney, 1995a).

A selection marker is usually employed, which may be part of the expression construct or separate from the expression construct (e.g., carried by the expression vector). The selection marker may be used as an alternative target locus for expression construct integration. Transformation of the host cells with the recombinant DNA molecules of the invention is monitored through the use of selectable markers. Examples of these are markers that confer resistance to antibiotics (e.g., bla confers resistance to ampicillin for *E. coli* host cells, nptII confers kanamycin resistance to *B. napus* cells) or that permit the host to grow on minimal medium (e.g., HIS4 enables *P. pastoris* GS115 His⁻ cells to grow in the absence of histidine). Selectable markers are usually associated with transcriptional and translational initiation and termination regulatory regions different from the expression construct in order to allow for independent expression of the marker. Where antibiotic resistance is employed, the concentration of the antibiotic for selection will vary depending upon the antibiotic, generally ranging between 10 and 500 µg of the antibiotic/mL of medium.

The expression construct is assembled by employing known recombinant DNA techniques. Restriction enzyme digestion and ligation are the basic steps employed to join two fragments of DNA. The ends of the DNA fragment may require modification prior to ligation and this may be accomplished by filling in overhangs, deleting terminal portions of the fragment(s) with nucleases (e.g., ExoIII), site directed mutagenesis, and adding new base pairs by the Polymerase Chain Reaction (PCR). Polylinkers and adaptors may be employed to facilitate joining of select fragments. The expression construct is typically assembled in stages employing rounds of restriction, ligation and transformation of *E. coli*. There are numerous cloning vectors available for construction of the expression construct and the particular choice is not critical to this invention. The selection of cloning vector will be influenced by the gene transfer system selected for introduction of the expression construct into the host cell. At the end of each stage, the resulting construct may be analyzed by restriction, DNA sequencing, hybridization and PCR analyses.

The expression construct may be transformed into the host as the cloning vector construct, either linear or circular, or may be removed from the cloning vector and used as is or introduced onto a delivery vector. The delivery vector facilitates the introduction and maintenance of the expression construct in the selected host cell type. The expression construct is introduced into the host cells by employing any of a number of gene transfer systems (e.g., natural competence, chemically mediated transformation, protoplast transformation, electroporation, biolistic transformation, transfection, or conjugation) and is dependent upon the host cells and vector systems used.

For instance, the expression construct can be introduced into *P. pastoris*, cells by protoplast transformation or electroporation. Electroporation of *P. pastoris* is easily accomplished and yields transformation efficiencies comparable to spheroplast transformation. Pichia cells are washed with sterile water and resuspended in a low conductivity solution (e.g., 1 M sorbitol solution). A high voltage shock applied to the cell suspension creates transient pores in the cell membrane through which the transforming DNA (e.g., expression construct) enters the cells. The expression construct is stably maintained by integration, through homologous recombination, into the axo1 (alcohol oxidase) locus.

Alternatively, an expression construct, comprising the sacB promoter and signal sequence operably linked to the protein coding sequence, is carried on a plasmid, pUB110, capable of autonomously replicating in *B. subtilis* cells. The resulting plasmid construct is introduced into *B. subtilis* cells by transformation. *Bacillus subtilis* cells develop natural competence when grown under nutrient poor conditions.

Host cells carrying the expression construct (i.e., transformed cells) are identified through the use of the selectable marker carried by the expression construct or vector and the presence of the gene of interest confirmed by a variety of techniques including hybridization, PCR, and antibodies.

Transformed microbial cells may be grown by a variety of techniques including batch and continuous fermentation on solid or semi-solid media. Transformed cells are propagated under conditions optimized for maximal product to cost ratios. Product yields may be dramatically increased through the manipulation of cultivation parameters such as temperature, pH, aeration and media composition. Careful manipulation and monitoring of the growth conditions for recombinant hyper-expressing *E. coli* cells may result in culture biomass and protein yields of 150 g (wet weight) of cells/L and 5 g of insoluble protein/L, respectively. Low concentrations of a protease inhibitor (e.g., phenylmethylsulfonyl fluoride or pepstatin) may be employed to reduce proteolysis of the over-expressed peptide or protein. Alternatively, protease-deficient host cells may be employed to reduce or eliminate degradation of the desired protein.

Following fermentation, the microbial cells may be removed from the medium through downstream processes such as centrifugation and filtration. If the desired product is secreted, it can be extracted from the cell free nutrient medium. Alternatively, the culture or cell free medium may be used directly or concentrated (e.g., ultrafiltration, dehydration, lyophilization) and used in an application requiring xylanase activity. In the case of intracellular production, the cells may be harvested and used directly or ruptured (e.g., mechanical forces, ultrasound, enzymes, chemicals, high pressure). The resulting lysate may be used as in an application requiring xylanase activity or subjected to further processing.

In a third example, *Brassica napus* cells are transformed by Agrobacterium-mediated transformation. The expression construct is inserted onto an binary vector capable of replication in *A. tumefaciens* and mobilization into plant cells. The resulting construct is transformed into *A. tumefaciens* cells carrying an attenuated Ti or "helper" plasmid. When leaf disks are infected with the recombinant *A. tumefaciens* cells, the expression construct is transferred into *B. napus* leaf cells by conjugal mobilization of the binary vector::expression construct. The expression construct integrates at random into the plant cell genome.

After selection and screening, transformed plant cells can be regenerated into whole plants and varietal lines of transgenic plants developed and cultivated using known methods.

Xylanase may be extracted from harvested portions or whole plants by grinding, homogenization, and/or chemical treatment. The use of seed specific lipophilic oleosin::gene fusions can facilitate purification by partitioning the oleosin fusion protein in the oil fraction of crushed canola seeds and away from the aqueous proteins (van Rooijen and Moloney, 1995a).

Expression of xylanases of the present invention in *Brassica napus* (canola) is useful, particularly as the enzyme will be expressed in every seed of the plant. Canola is an important agricultural crop due to its high oil content. There are many uses for canola oil, including such diverse applications as lubricating oils and oils for human consumption. The non-oil fraction remaining after the oil is extracted from canola seeds by techniques such as crushing may be described as canola meal. Canola meal is typically used as an animal feed supplement due to its high protein content, which may be as high as 40–50%. Canola meal makes an ideal feed supplement as it is substantially less expensive than alternatives such as soybean meal. Furthermore, canola meal also contains higher concentrations than soybean meal of nutrients such as carbohydrates.

The oil in the seeds of *B. napus* is found within oil-bodies surrounded by an oil-body membrane which functions to contain the oil. Oleosin proteins are located in the membrane surrounding the oil body. Oleosins (oil-body proteins) are structural proteins found in the seeds of all higher plants investigated to date (monocots, dicots and gymnosperms). They are highly lipophilic with a unique secondary structure which permits their central core to be embedded in oil-bodies while the more hydrophilic N- and C-termini reside on the cytoplasmic side. Their role appears to be primarily that of stabilizing triacylglyceride-containing oil-bodies as discrete organelles (van Roijen and Moloney, 1995a). The hydrophilic N- and C-termini of the oleosin protein may provide attachment sites for forming fusions with other proteins.

In a preferred embodiment of the present invention, *B. napus* is transformed with an expression construct containing a nucleotide sequence encoding a xylanase of the present invention translationally fused to a nucleotide sequence encoding an oleosin protein to provide seed oil body expression of the xylanase, as described in the examples which follow.

The oleosin-xylanase fusion protein is immobilized in the seed oil-body membrane and remains with the canola meal portion during oil extraction. As demonstrated in the examples which follow, the oleosin-xylanase fusion proteins retain xylanase activity. Canola meal produced from the transgenic *B. napus* of the present invention thus provides an ideal source of xylanase when the canola meal is used as a feed supplement (protein source) in animal diets. Supplemental xylanase in animal diets degrades cell wall components in the animal feed, resulting in increased feed digestion and a reduction in pollution from animal wastes.

If necessary, various methods for purifying the xylanase, from microbial fermentation and plant extracts, may be employed. These include precipitation (e.g., ammonium sulfate precipitation), chromatography (gel filtration, ion exchange, affinity liquid chromatography), ultrafiltration, electrophoresis, solvent—solvent extraction (e.g., acetone precipitation), combinations thereof, or the like.

All or a portion of the microbial cultures and plants may be used directly in applications requiring the action of a xylanase. Various formulations of the crude or purified xylanase preparations may also be prepared. The xylanase can be stabilized through the additions of other proteins (e.g., gelatin, skim milk powder) and chemical agents (e.g., glycerol, polyethylene glycol, reducing agents and aldehydes). Enzyme suspensions can be concentrated (e.g., tangential flow ultrafiltration) or dried (spray and drum drying, lyophilization) and formulated as liquids, powders, granules and gels through known processes.

Formulations of the desired product may be used directly in applications requiring the action of a xylanase. Liquid concentrates, powders and granules may be added directly to reaction mixtures and fermentations. The formulated xylanase can be administered to animals in drinking water. It may be mixed also with, sprayed on or pelleted with other feed stuffs through known processes. Alternatively, the xylanase gene may be introduced into an animal, thereby eliminating the need for the addition of supplemental xylanase.

In another formulation, the xylanase of the present invention may take the form of viable microbial feed inoculants. Cultures of microorganisms expressing a xylanase gene, such as *N. patriciarum* strain 27, or recombinant microorganisms expressing the xylanase CDS are grown to high concentrations in fermentors and then harvested and concentrated by centrifugation. Food-grade whey and/or other cryoprotectants are then admixed with the cell concentrate. The resulting mixture is then cryogenically frozen and freeze dried to preserve xylanase activity by standard lyophilization procedures. The freeze-dried culture may be further processed to form finished product by such further steps as blending the culture with an inert carrier to adjust the strength of the product.

All or a portion of the microbial cultures and plants as produced by the present invention may also be used in a variety of industrial processes requiring the action of a xylanase.

Examples of such applications are in the production of feed ingredients and feed additives for livestock production, the retting of flax fibers, the clarification of fruit juices, the preparation of dextrans for use as food thickeners and the production of fluids and juices from plant materials. Xylanases can be used also in the bioconversion involving the hydrolysis of xylan to xylooligosaccharides and xylose and biopulping to treat cellulose pulps to remove xylan impurities to produce pulps with different characteristics.

EXAMPLES

Example 1

Cloning an Endo-xylanase Gene from *Neocallimastix patriciarum*

*Neocallimastix patriciarum* strain 27 was cultivated anaerobically at 39° C. in a modified semi-defined medium (Lowe et al., 1985) containing either Whatman No. 1 filter paper or 0.15% glucose as a carbon source. Cells were harvested by centrifugation after 4 d growth, resuspended in extraction buffer (25 mM Tris-HCl, pH 8.0; 10 mM EDTA; 50 mM glucose) and stored at −70° C. overnight. The preparation was thawed at room temperature and homogenized until all cells were resuspended. Sodium dodecyl sulfate (SDS) and diethylpyrocarbonate (DEPC) were added to final concentrations of 0.5% (w/v) and 25 mM respectively. The suspension was incubated at 37° C. for 1 h. Proteinase K (0.1 mg/mL) was added, and the mixture was incubated for 1 h at 55° C., extracted twice with phenol and twice with phenol/chloroform. The DNA was precipitated with ethanol, and the resulting DNA pellet resuspended in TE (10 mM Tris, pH 8.0; 1 mM EDTA) buffer.

*Neocallimastix patriciarum* strain 27 genomic DNA was partially digested by EcoRI. Agarose gel purified 4- to 7-kb EcoRI fragments were ligated (overnight, 4° C.) to EcoRI-cut and dephosphorylated λgtWESλB arms at a molar ratio of 1:2. The ligated DNA was packaged with a λ DNA in vitro packaging kit. The phage library was amplified on TN plates (10 g Bacto-tryptone, 5 g NaCl per litre containing 0.2% maltose and 10 mM MgCl2, pH 7.5) with *Escherichia coli* ED8654 as the host bacterium.

Recombinant phage were screened for xylanase activity by overlaying plaques with 0.7% (w/v) agarose containing 0.1–0.25% (w/v) water soluble oat spelt xylan dissolved in 25 mM potassium phosphate buffer (pH 6.5). The plates were incubated at 39° C. for 3–18 h and stained with a 0.1% (w/v) aqueous solution of Congo red and destained with 1 M NaCl. Xylanase-producing plaques were surrounded by a yellow halo visible against the red background. Two positive clones were recovered after screening 50,000 plaques. Positive plaques were picked and resuspended in SM buffer (Sambrook et al., 1989). The plaques were purified three successive times by isolation from agar plates.

Example 2

Characterization of Positive Endo-xylanase Clones

Phage stocks and DNA were prepared according to methods described by Sambrook et al. (1989). Restriction analyses determined that the two positive clones carried identical 6.5-kb EcoRI inserts. This clone was designated λNspX-101. The location of the endo-xylanase gene on the 6.5-kb EcoRI fragment was narrowed down by subcloning fragments of the 6.5-kb EcoRI fragment onto a number of cloning vectors including pBR322 (Bethesda Research Laboratories—BRL, Mississauga, ON), pUC18 (BRL) or pBluescriptIISK+(Stratagene Cloning Systems, La Jolla, Calif.). *Escherichia coli* HB101 and DH5α (BRL) were used as the host bacteria for the various cloning vectors. Transformed cells were propagated at 37° C. in Luria-Bertani (LB) medium (Sambrook et al., 1989). Ampicillin (100 μg/mL) was incorporated into media used to culture plasmid-bearing *E. coil* strains. Transformant colonies were cultivated on LB medium containing 0.1–0.25% oat spelt xylan. Xylanase activity was detected by staining plates with Congo red.

Figure 2:
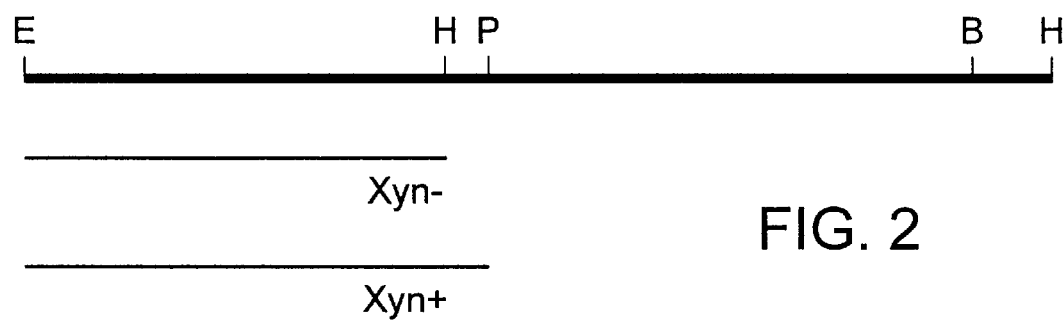
FIG. 2 is a schematic representation of the deletion analysis in which the location of the endo-xylanase gene cloned from *N. patriciarum* 27 was determined. E=EcoRI; H=HindIII; P=PvuII; B=BglII. p FIGS. 3A–3C provide the nucleotide sequence of a fragment containing the endo-xylanase gene (xynC) cloned from *N. patriciarum* 27. The predicted amino acid sequence is shown beneath the nucleotide sequence. The CDS is located from nucleotide 301 to nucleotide 1755.
Figure 4A:
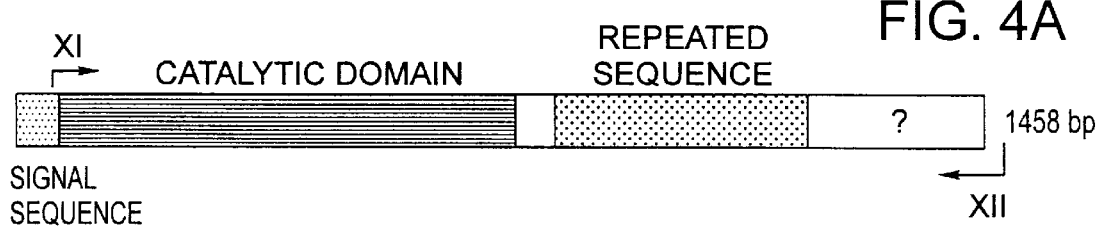
FIG. 4A is a schematic representation of the structure of the xynC coding region. The signal sequence is followed by the sequence encoding for the catalytic domain of the enzyme (solid box) and a repeated peptide (shaded box). The 3' end of the gene codes for a region of unknown function.
Figure 4B:
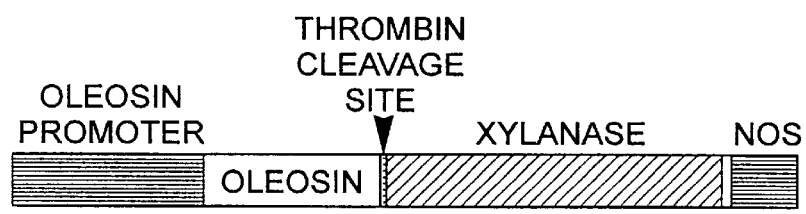
FIG. 4B illustrates the oleosin-xylanase C expression construct. The endo-xylanase gene was ligated between the oleosin gene (promoter plus coding region) and the terminator of nopaline synthetase (NOS).

The 6.5-kb EcoRI insert from λNspX-101 was subcloned into pBR322 yielding plasmid pNspX-01 (FIG. 1). The 1.7- and 2.2-kb HindIII fragments from pNspX-01 were cloned in the correct orientation into pBR322 to produce pNspX-02. The 4.3-kb BamHI-EcoRI fragment from pNspX-02 was ligated with BamHI-EcoRI digested pUC18. The resulting plasmid was designated pNspX-04 (FIG. 1). Deletion of the SanI fragment from pNspX-04 produced pNspX-06. Further truncation of the 3.6-kb EcoRI-SalI fragment contained on pNspX-06 was accomplished by subcloning the EcoRI-PvuII or EcoRI-HindIII fragments on to pBluescriptSKII+ (Stratagene Cloning Systems). Xylanase activity was observed only for the clone carrying the EcoRI PvuII fragment thereby suggesting that the HindIII site was located within the endo-xylanase gene (FIG. 2).

The origin of the endo-xylanase gene was confirmed by Southern blot hybridization using the 3.5-kb ClaI fragment from pNspX-02, labelled with [α-$^{32}$P]-dCTP, as a probe (Tamblyn Lee et al., 1993).

Example 3
Biochemical Characteristics of the Cloned *Neocallimastix patriciarum* Endo-xylanase The cloned endo-β-1,4-xylanase was secreted into the periplasmic space of host *Eschedchia coli* (pNspX-06) cells. The biochemical characteristics of the cloned enzyme were determined using crude extracts containing periplasmic endo-xylanase released by osmotic shock (Table 1, Tamblyn Lee et al., 1993). Xylanase activity was determined by measuring the amount of reducing sugars released from substrates according to the method of Nelson-Somogyi (Somogyi, 1952). The *N. patriciarum* endo-xylanase hydrolyzed oat spelt xylan and birch wood xylan almost equally well, but exhibited very low activity on arabinoxylan. The pH and temperature optima for the periplasmic endo-xylanase activity were 6.2 and 40° C., respectively, and the $K_m$ for oat spelt xylan hydrolysis was 0.89 mg/mL. SDS-PAGE followed by zymogram analysis showed active bands of 68, 58, and 51 kDa. The isoelectric point, determined by isoelectric focusing combined with zymogram analysis, was 3.6.

TABLE 1

General biochemical properties of the *N. patriciarum* 27 xylanase

| Property | |
|---|---|
| Molecular weight (kDa) | 68/58/51 |
| Isoelectric point | 3.6 |

TABLE 1-continued

General biochemical properties of the *N. patriciarum* 27 xylanase

| Property | |
|---|---|
| pH optimum | 6.2 |
| Temperature optimum | 40° C. |
| Substrate specificity | |
| Oat spelt xylan | +++++ |
| Birch wood xylan | +++++ |
| Rye flour arabinoxylan | +/− |
| Carboxymethylcellulose | ++ |
| Acid-swollen cellulose | +/− |
| Barley β-glucan | +/− |
| Lichenan | − |
| $K_m$ (mg oat spelt xylan/ml) | 0.89 |

Example 4
Nucleotide Sequence and Structural Analyses of the *Neocallimastix patriciarum* Endo-xylanase Gene The 3.4-kb EcoRI-BglII fragment of pNspX-06 was sequenced in both strands. Samples were prepared for DNA sequence analysis on an Applied Biosystems Model 373A DNA sequencing system (Applied Biosystems, Inc., Mississauga, ON) by using a Taq DyeDeoxy™ Terminator Cycle Sequencing Kit (Applied Biosystems, Inc.). Template DNA was extracted from overnight cultures of *E. coli* DH5α (pNspX-06) with the Wizards™ minipreps DNA purification system (Promega Corp., Madison, Wis.). Overlapping sequences were generated by primer walking. The DNA sequence data was analyzed using MacDNASIS DNA software (Hitachi Software Engineering Co., Ltd., San Bruno, Calif.).

DNA structural analysis identified a single 1458 bp open reading frame (ORF), designated xynC, overlapping the HindIII and PvuII sites of the 3.4 kb EcoRI-BglII insert and large enough to encode a 51 kDa endo-xylanase (FIGS. 3A–3C). Translation of the ORF would result in the expression of a 485 amino acid polypeptide with a predicted molecular weight of 50.4 kDa. Further analyses identified a putative signal sequence (nucleotides 301–360, FIGS. 3A–3C, 4A, and 4B) followed by a catalytic domain. The N-terminal catalytic domain is followed by a putative proline rich, highly reiterated linker region and a region of unknown function.

Figure 5:
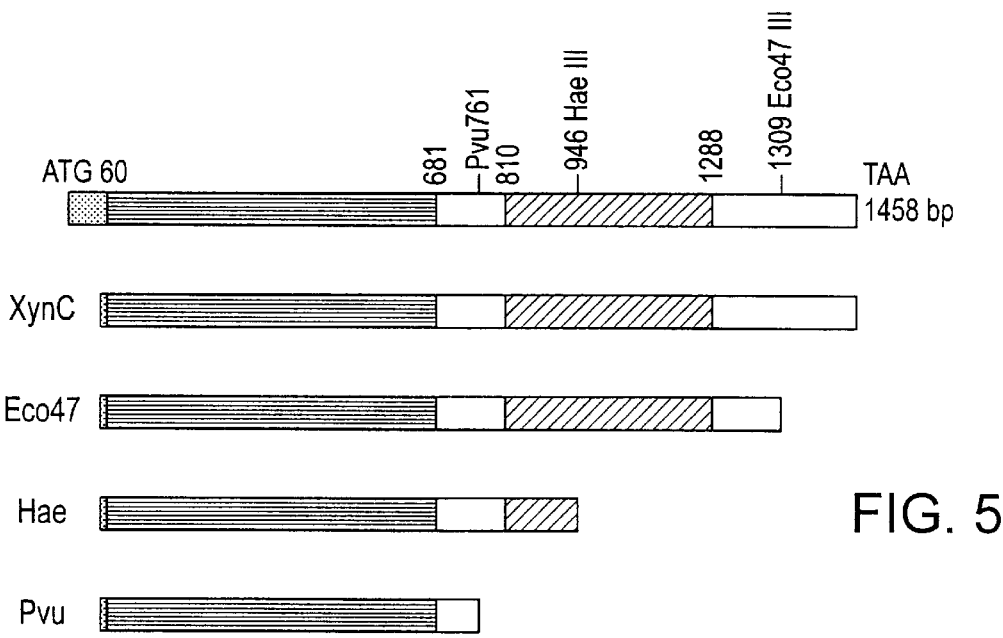
FIG. 5 is a schematic representing the *N. patriciarum* endo-xylanase gene (xynC) fragments cloned into pGEX-4T-3. (Pvu-PvuII)

The extent of the endo-xylanase catalytic domain was determined by deletion analysis. The coding sequence of xynC encoding sequence less the first 41 nucleotides (nt 301–341, FIG. 3A) was amplified by PCR with oligonucleotide primers XI (ATC TCT AGA ATT CAA CTA CTC TTG CTC AAA G; SEQ ID NO. 3) and XII (GGG TTG CTC GAG ATT TCT AAT CAA TTT AT; SEQ ID NO. 4). The oligonucleotides were designed to place an EcoRI site at the 5' end and a XhoI site at the 3' end of the PCR product. This enabled the xynC PCR product (FIG. 4A) to be cloned as a translational fusion into EcoRI XhoI digested pGEX-4T-3 (Pharmacia Biotech Inc., Baie D'Urfe, PQ). *Escherichia coli* cells transformed with this construct, named pGEXxynC, produced endo-xylanase activity. A series of 3' deletions to xynC was also constructed in pGEX-4T-3 (FIG. 5). Fusion proteins (glutathione S-transferase::xylanase C) were expressed and affinity purified on glutathione Sepharose 4B according to the GST gene fusion system manual (Pharmacia Biotech Inc.). Bound fusion protein was either eluted and used directly in xylanase assays (GST-fusions) or cleaved with thrombin to release only the xynC-encoded peptides. The specific activities of the purified GST-fusions and cleaved xylanase C peptides were determined. Protein concentration was measured with a BioRad (BioRad Laboratories Canada Ltd., Mississauga, ON) protein assay kit. Protein samples were added to a 50 mM potassium phosphate buffer (pH 6.5) containing 1.5% oat spelt xylan. Samples were incubated at 40° C. Xylanase activity was determined by measuring the amount of reducing sugar released from the substrate (Somogyi, 1952). All truncated proteins tested (FIG. 5, Table 2) had lower specific activities (Table 2) indicating that the full length xylanase C is required for maximal activity. The reduction in activity was particularly pronounced in the case of the Pvu fusion protein. This construct displayed only 1.2% of the activity of the full length GST-XynC fusion protein. By comparison the cleaved Pvu xylanase C protein retained three quarters of the full length protein activity (Table 2).

The specific activity of cleaved affinity purified xylanase C was determined to be 555 units of endo-xylanase activity/mg of protein. One unit of endo-xylanase activity was defined as one μmol of reducing sugar equivalents released per minute.

TABLE 2

Relative xylanase activity (%) of truncated xylanase C proteins.

| Treatment | Construct | Relative xylanase activity |
|---|---|---|
| Cleaved | XynC | 100.0 |
|  | Eco47 | 80.2 |
|  | Hae | 85.3 |
|  | Pvu | 74.8 |
| GST-fusion | XynC | 100.0 |
|  | Pvu | 1.2 |

Example 5
Overexpression of the *Neocallimastix patriciarum* Endo-xylanase Gene

Isolation and characterization of xynC from *N. patriciarum* 27 enables the large scale production of Xylanase C in any of a number of prokaryotic (e.g., *E. coli* and *B. subtilis*) or eukaryotic (e.g., fungal—Pichia, Saccharomyces, Aspergillus, Trichoderma; plant—Brassica, Zea, Solanum; or animal—poultry, swine or fish) expression systems using known methods. For example, general teachings for the construction and expression of xynC in *E coli, P. pastoris*, and *B. napus* are provided below. Similar approaches may be adopted for expression of the *N. patriciarum* 27 endo-xylanase in other prokaryotic and eukaryotic organisms.

A. Cloning of the *Neocallimastix patriciarum* xynC in an *Escherichia coli*-specific Expression Construct An expression construct is constructed in which the region encoding the full length xylanase C, less amino acids 1–14 (FIGS. 3A–3C) is transcriptionally fused with the tac promoter (Brosius et al., 1985). The promoter sequences may be replaced by those from other promoters that provide for efficient expression in *E. coli*. The expression construct is introduced into *E. coli* cells by transformation.

i. Construction of the *E. coli* expression vector

A number of *E. coli* expression vectors based on the tac or related promoters are commercially available. The construct may be prepared with pKK223-3 available from Pharmacia Biotech Inc. The region of xynC encoding the XynC protein (less amino acids 1–14) is amplified with oligonucleotide primers XIII (SEQ ID NO.5-GC GAA TTC ATG TCA ACT CTT GCT CAA AGT TTC) and XIV (SEQ ID NO. 6-GCC TGC AGT GAT TTC TAA TCA ATT TAT). The oligonucleotides XIII (SEQ ID NO. 5) and XIV (SEQ ID NO. 6) were designed to insert suitable restriction sites at the PCR product's termini to allow direct assembly of the amplified product with pKK223-3. The region of xynC amplified with XIII (SEQ ID NO. 5) and XIV (SEQ ID NO. 6) is digested with EcoRI and PstI and ligated into similarly cleaved pKK223-3.

ii. Transformation of *E. coil* and XylanaseC expression

The pKK223-3::xynC ligation mix is used to transform competent *E. coli* cells. Strains suitable for high levels of protein expression, such as SG13009, CAG926 or CAG929 (carrying lacd on a plasmid such as pREP4), are employed. Transformed cells are spread on LB agar containing ampicillin (100 μg/mL) and incubated overnight at 37° C. Ampicillin resistant colonies are screened for the presence of the desired pKK223-3::xynC construct by extracting pDNA and subjecting the pDNA to agarose gel electrophoresis and restriction analysis. Positive clones are further characterized by PCR and nucleotide sequence analysis.

Expression of the *N. patriciarum* 27 xylanase by transformed *E. coli* cells is tested by growing the cells under vigorous aeration at 37° C. in a suitable liquid medium (e.g., LB or 2xYT) containing the appropriate antibiotic selection until the optical density (600 nm) is between 0.5 and 1.0. The tac promoter is induced by adding isopropyl-β-D-thiogalactoside (IPTG) to a final concentration between 0.1 and 2 mM. The cells are cultivated for an additional 2 to 4 h and harvested by centrifugation. Protein expression is monitored by SDS-PAGE, and western blot/immunodetection techniques.

The expressed XynC can be extracted by breaking (e.g., sonication or mechanical disruption) the *E. coli* cells. Protein inclusions of XynC can be harvested by centrifugation and solubilized with 1 to 2% SDS. The SDS can be removed by dialysis, electroelution or ultrafiltration. The xylanase activity of prepared cell extracts may be assayed by standard methods described in Example 4.

B. Cloning of the *Neocallimastix patriciarum* Endo-xylanase in a *Pichia pastoris*-specific Expression Construct An expression construct is constructed in which the region encoding the full length xylanase C, less amino acids 1–14 (FIGS. 3A–3C) is translationally fused with the secretion signal sequences found on *P. pastoris* expression vectors (Pichia Expression Kit Instruction Manual, Invitrogen Corporation, San Diego, Calif.) in order to express the *N. patriciarum* xylanase as a secreted product. The promoter and secretion signal sequences may be replaced by those from other promoters that provide for efficient expression in Pichia. The expression construct is introduced into *P. pastoris* cells by transformation.

i. Construction of the *P. pastoris* expression vector

A number of *P. pastoris* expression vectors based on the a1 promoters and α-Factor or pho1 signal sequences are commercially available. The construct can be prepared with pPICαB available from Invitrogen Corporation. The region of xynC encoding the XynC protein (less amino acids 1–14) is amplified with oligonucleotide primers XI (SEQ ID NO.3) and XII (SEQ ID NO. 4). The oligonucleotides XI (SEQ ID NO. 3) and XII (SEQ ID NO. 4) were designed to insert suitable restriction sites at the PCR product's termini to allow direct assembly of the amplified product with pPICαB. The region of xynC amplified with XI (SEQ ID NO. 3) and XII (SEQ ID NO. 4) is digested with EcoRI and XhoI and ligated into similarly cleaved pPICαB.

ii. Transformation of *P. pastoris* and XynC expression

The pPICαB::xynC ligation mix is used to transform competent *E coli* DH5α cells. Transformed cells are spread on LB agar containing ampicillin (100 μg/mL) and incubated overnight at 37° C. Ampicillin resistant colonies are screened for the presence of the desired pPICαB::xynC construct by extracting pDNA and subjecting the pDNA to agarose gel electrophoresis and restriction analysis. Positive clones are further characterized by PCR and DNA sequence analysis. Plasmid DNA is prepared from a 1 L culture of an *E. coli* clone carrying the desired pPICαB::xynC construct. The pDNA is digested with PmeI and analyzed by agarose gel electrophoresis to confirm complete digestion of the vector. The digested pDNA is extracted with phenol:chloroform, ethanol precipitated and resuspended in sterile distilled H$_2$O to a final concentration of 1 µg/µL. In preparation for transformation, *P. pastoris* GS115 or KM71 cells are grown for 24 h at 30° C. in YPD broth. Cells from a 100 µL of culture are harvested by centrifugation and resuspended in 100 µL of transformation buffer (0.1M LiCl, 0.1M dithiothreitol, 45% polyethylene glycol 4000) containing 10 µg salmon sperm DNA and 10 µg of linearized pPICαB::xynC. The mixture is incubated for 1 h at 37° C., spread on YPD minimal agar medium containing zeocin (100 µg/ml) and incubated for 2 to 5 d at 30° C. Colonies growing on the selective medium are streaked for purity and analyzed for the presence of the integrated xynC by PCR and Southern blot hybridization.

Expression of the *N. patriciarum* 27 xylanase by transformed *P. pastoris* cells is tested by growing the cells at 30° C. and under vigorous aeration in a suitable liquid medium (eg., buffered complex glycerol media such as BMGY) until a culture optical density (600 nm) of 2 to 6 is reached. The cells are harvested and resuspended to an OD$_{600}$ of 1.0 in an inducing medium (e.g., buffered complex methanol medium, BMMY) and incubated for a further 3 to 5 days. Cells and cell free culture supernatant are collected and protein expression is monitored by enzyme assay, SDS-PAGE, and western blot/immunodetection techniques.

C. Cloning of the *Neocallimastix patriciarum* Endo-xylanase in a *Brassica napus* Seed-specific Expression Construct Transformation and gene expression methods have been developed for a wide variety of monocotyledonous and dicotyledonous crop species. In this example, a *N. patriciarum* 27 xylanase expression construct was constructed in which the region encoding the full length xylanase C, less amino acids 1–14 (FIGS. 3A–3C) is translationally fused with an oleosin coding sequence in order to target seed oil body specific expression of the *N. patriciarum* xylanase. The promoter and/or secretion signal sequences may be replaced by those from other promoters that provide for efficient expression in *B. napus* or any other transformable plant species in order to achieve the same goal as is the objective of this invention. The expression construct is introduced into *B. napus* cells by Agrobactetium mediated transformation.

i. Construction of the *B. napus* expression vector

A number of expression vectors functional in *B. napus* are described in the literature (Gelvin et al., 1993). To construct a oleosin-xylanase gene fusion, the oleosin and recombinant xync genes were first cloned into pBluescriptIIKS+(pBS) to create an intermediate plasmid. The construct pCGYOBP-GUSA (van Rooijen and Moloney, 1995b) was digested with PstI and BamHI to isolate the 1608-bp fragment containing the oleosin promoter and oleosin coding region. The xynC coding region was obtained by the digestion of pGEXxynC with BamHI and XhoI. These two fragments were cloned into pBS previously digested with PstI and XhoI. The resulting plasmid was designated as pBSoleXyn. To obtain a nopaline synthetase (NOS) terminator sequence flanked by XbaI and XhsI restriction sites, a BamHI and HindIII fragment from pCGYOBPGUSA was subcloned into pBS to make an intermediate plasmid pBSNos. Digestion of this construct with Xba I and XhoI liberated a XbaI XhoI flanked fragment containing the NOS terminator. The oleosin-xylanase C expression construct was assembled in pCGNa 559 (McBride and Summerfelt, 1990). The oleosin-xynC gene fusion was cut out of pBSoleXyn with Psi and XhoI. This fragment was ligated with the XbaI XhoI flanked NOS fragment from pBSNos and PstI XhoI digested pCGN1559. This plasmid was named pCGOleXyn.

ii. Transformation of *B. napus* and stable xylanase C expression

Transgenic *B. napus* were prepared as described by van Rooijen and Moloney (1995a; 1995b). *Agrobacterium tumefaciens* strain EHA101 was transformed by electroporation with pCGOleXyn. Cotyledonary petioles of *B. napus* were transformed with *A. tumefaciens* EHA101 (pCGOleXyn). Transgenic plants were regenerated from explants that rooted on hormone-free MS medium containing 20 µg/mL kanamycin. Young plants were assayed for NPTII activity, grown to maturity and allowed to self pollinate and set seed. Seeds from individual transformants were pooled and the presence of xynC was confirmed by PCR and Southern blot hybridization. XynC production was confirmed by western blot immunodetection with polyclonal antibodies specific for this protein. Part of the seed sample was assayed for xylanase activity, and compared to seeds from untransformed plants (Table 3). Oil bodies were isolated from mature dry seeds by the method described in van Rooijen and Moloney (1995a). Oil bodies were suspended in 50 mM potassium phosphate buffer (pH 4.5). Xylanase assays were performed as described in Example 4. Transgenic plants carrying the oleosin-xylanase C construct produced 10 to 50 times higher levels of xylanase activity than the wild type control plants.

The application of transgenic oil-bodies as an immobilized matrix was tested as described in van Rooijen and Moloney (1995a). Oil-bodies carrying oleosin-xylanase C fusion protein (0.1 mL) were mixed with 0.2 mL of substrate mix containing 0.5% RBB-xylan in a 50 mM potassium-phosphate buffer (pH 6.5). The reaction mixtures were incubated for 60 min at 40° C. After each incubation, the reaction mix was centrifuged to separate oil-bodies and aqueous substrate. The "unternatant" was then removed and the oil pad was recycled in a new reaction through the addition of fresh substrate. The unternatant was assayed for RBB-xylan digestion by the method of Biely et al. (1988). Absolute ethanol (0.8 mL) was added to the unternatant samples to stop the xylanase reactions. The samples were allowed to stand at room temperature for 30 min and centrifuged for 5 min in a microfuge to remove the precipitated substrate. The absorbances of the resulting supernatants were measured at 595 nm. The transgenic oil-bodies retained their endo-xylanase activity through four rounds of recycling (Table 4). These results clearly demonstrated the stability and potential of transgenic oil-bodies as an immobilized enzyme matrix.

TABLE 3

Xylanase activity of recombinant oil-bodies extracted from transgenic canola carrying the oleosin-xylanase C expression construct.

| Transgenic Line | Xylanase activity | |
|---|---|---|
| | nmol/min/mg | (standard error) |
| Wild type | 0.413 | (0.31) |
| T1 | 18.78 | (2.63) |
| T4 | 29.19 | (8.39) |
| T7 | 22.85 | (0.42) |
| T13 | 6.68 | (0.76) |
| T18 | 12.23 | (1.74) |
| T23 | 5.86 | (0.84) |

TABLE 4

Xylanase activity of recycled oil-bodies

| Number of cycles | Relative xylanase activity |
|---|---|
| 1 | 100.0 |
| 2 | 152.5 |
| 3 | 154.0 |
| 4 | 148.5 |

Example 6
Identification of Related Xylanase Genes in Other Microorganisms

To identify a xylanase gene related to xynC, hybridization analysis can be used to screen nucleic acids from other organisms of interest using xynC (SEQ ID NO. 1) or portions thereof as probes by known techniques (Ausubel et al., 1990, Sambrook et al., 1989). Related nucleic acids can be cloned by employing techniques known to those skilled in the art. Radioisotopes (i.e., $^{32}P$) may be required when screening organisms with complex genomes in order to increase the sensitivity of the analysis. Polymerase Chain Reaction (PCR) amplification may also be used to identify genes related to xynC. Related sequences found in pure or mixed cultures are preferentially amplified by PCR (and variations of such as Reverse Transcription—PCR) with oligonucleotides primers designed using SEQ ID NO. 1. Amplified products may be visualized by agarose gel electrophoresis and cloned using techniques know to those skilled in the art.

A variety of materials, including cells, colonies, plaques, and extracted nucleic acids (e.g., DNA, RNA), may be examined by these techniques for the presence of related sequences.

All publications mentioned in this specification are indicative of the level of skill of those skilled in the art to which this invention pertains. All publications are herein incorporated by reference to the same extent as if each individual publication was specifically and individually indicated to be incorporated by reference.

Although the foregoing invention has been described in some detail by way of illustration and examples for purposes of clarity and of understanding, it will be obvious that certain changes and modifications may be practiced within the scope of the appended claims.

REFERENCES

Current Protocols in Molecular Biology (1990), Ausubel, F. A. et al., (eds.) Green Publishing and Wiley-Interscience, New York.

Biely, P., D. Mislovicová and R. Toman (1988) Methods Enzymol. 160:536–542.

Brosius, J., M. Erfl and J. Storella (1985) J. Biol. Chem. 260:3539–3541.

Chesson, A., C. W. Forsberg, and E. Grenet (1995) In: Recent developments in the nutrition of herbivores. Proceedings of the IVth International Symposium on the Nutrition of Herbivores, M. Journet, E. Grenet, M-H. Farce, M. Theriez, C. Demarquilly (eds,) INRA Editions, Paris. pp. 249–277.

Ellis, S. B., et al. (1985) Mol. Cell. Biol. 5:1111–1121.

Plant Molecular Biology Manual (1993) Gelvin, S. B., et al. (eds.) Kluwer Academic Publishers, Boston, Mass.

Hodgson J. (1994) Bio/Technology 12: 789–790

Lowe, S. E., et al. (1985) J. Gen. Microbiol. 131:2225–2229.

McBride, K. E. and K. R. Summerfelt (1990) Plant Mol. Biol. 15:269–276.

McNeil M., et al. (1984) Ann Rev Biochem 53:625–663

Molecular cloning. A laboratory manual (1989) 2nd ed. Sambrook, J., E. F. Fritsch, and T. Maniatis, eds. Cold Spring Harbor Laboratory Press. Cold Spring Harbor, N.Y.

Somogyi, M. J. (1952) J. Biol. Chem. 195:19–23.

Tamblyn Lee, J. M., et al. (1993) Can J. Microbiol. 39:134–139.

Teather, R. M. and P. J. Wood (1982) Appl. Environ. Microbiol. 43:777–780.

van Rooijen, G. J. H. and M. M. Moloney. (1995)a Bio/Technology 13:72–77.

van Rooijen G. J. H. and M. M. Moloney. (1995)b Plant Physiol 109:1353–1361

Wong, S.-L. (1989) Gene 83:215–223.

We claim:

1. A transgenic plant transformed with a DNA molecule comprising a xylanase coding region that encodes a xylanase obtained from a strain of the species *Neocallimastix patriciarum* so that said encoded xylanase can be expressed by said plant, said xylanase coding region being capable of hybridizing under conditions of medium stringency with a first probe comprising at least 25 continuous nucleotides of the complement of the nucleotide sequence depicted in SEQ ID NO:1 from nucleotide 360 to nucleotide 1063, and with a second probe comprising at least 25 continuous nucleotides of the complement of the nucleotide sequence depicted in SEQ ID NO:1 from nucleotide 1063 to nucleotide 1755.

2. A transgenic plant according to claim 1, said encoded xylanase comprising the amino acid sequence depicted in SEQ ID NO:2 from amino acid 21 to amino acid 255.

3. A transgenic plant according to claim 1, said encoded xylanase comprising the amino acid sequence depicted in SEQ ID NO:2 from amino acid 21 to amino acid 315.

4. A transgenic plant according to claim 1, said encoded xylanase comprising the amino acid sequence depicted in SEQ ID NO:2 from amino acid 21 to amino acid 437.

5. A transgenic plant according to claim 1, said encoded xylanase comprising the amino acid sequence depicted in SEQ ID NO:2 from amino acid 21 to amino acid 485.

6. A transgenic plant according to claim 1, said encoded xylanase comprising the amino acid sequence depicted in SEQ ID NO:2.

7. A transgenic plant according to claim 1, said DNA molecule comprising the nucleotide sequence depicted in SEQ ID NO:1 from nucleotide 301 to nucleotide 1755.

8. A transgenic plant according to claim 1, further comprising an oleosin coding region that encodes an oleosin protein, said oleosin coding region being operably linked to said xylanase coding region to encode an oleosin-xylanase fusion protein, said plant being capable of expressing said oleosin-xylanase fusion protein.

9. A transgenic plant according to claim 1, said plant being *Brassica napus*.

10. A method for producing a transgenic plant capable of expressing a xylanase, comprising the steps of:

(a) transforming plant cells with a DNA molecule comprising a xylanase coding region that encodes a xylanase obtained from a strain of the species *Neocallimastix patriciarum*, said xylanase coding region being capable of hybridizing under conditions of medium stringency with a first probe comprising at least 25 continuous nucleotides of the complement of the nucleotide sequence depicted in SEQ ID NO:1 from nucleotide 360 to nucleotide 1063, and with a second probe comprising at least 25 continuous nucleotides of the complement of the nucleotide sequence depicted in SEQ ID NO:1 from nucleotide 1063 to nucleotide 1755; and, (b) regenerating mature plants from said transformed cells.

11. A method according to claim 10, said encoded xylanase comprising the amino acid sequence depicted in SEQ ID NO:2 from amino acid 21 to amino acid 255.

12. A method according to claim 10, said encoded xylanase comprising the amino acid sequence depicted in SEQ ID NO:2 from amino acid 21 to amino acid 315.

13. A method according to claim 10, said encoded xylanase comprising the amino acid sequence depicted in SEQ ID NO:2 from amino acid 21 to amino acid 437.-

14. A method according to claim 10, said encoded xylanase comprising the amino acid sequence depicted in SEQ ID NO:2 from amino acid 21 to amino acid 485.

15. A method according to claim 10, said encoded xylanase comprising the amino acid sequence depicted in SEQ ID NO:2.

16. A method according to claim 10, said DNA molecule comprising the nucleotide sequence depicted in SEQ ID NO:1 from nucleotide 301 to nucleotide 1755.

17. A method according to claim 10, said DNA molecule further comprising an oleosin coding region that encodes an oleosin protein, said oleosin coding region being operably linked to said xylanase coding region to encode an oleosin-xylanase fusion protein.

18. A method according to claim 10, said plant cells being *Brassica napus cells*.

* * * * *

UNITED STATES PATENT AND TRADEMARK OFFICE
CERTIFICATE OF CORRECTION

PATENT NO. : 6,137,032
DATED : October 24, 2000
INVENTOR(S) : Cheng et al.

It is certified that error appears in the above-identified patent and that said Letters Patent is hereby corrected as shown below:

Column 13,
Line 14, please replace "coil" with -- coli --.
Line 25, replace "SanI" with -- Sa/I --.
Line 42, please replace "Eschedchia" with -- Escherichia --.

Column 16,
Line 11, please replace "lacd" with -- lacl --.
Line 52, please replace "al" with -- aoxl --.

Column 17,
Line 67, please replace "XhsI" with -- Xhol --.

Column 18,
Lines 5-6, please replace "pCGNa559" with -- pCGN1559 --.
Line 7, please replace "pBSoleXyn with Psi" with -- pBSOleXyn with PstI --.

Signed and Sealed this

Thirteenth Day of May, 2003

JAMES E. ROGAN
*Director of the United States Patent and Trademark Office*

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 2058 base pairs
      (B) TYPE: nucleic acid
      (C) STRANDEDNESS: double
      (D) TOPOLOGY: linear (ii) MOLECULE TYPE: DNA (genomic)

(iii) HYPOTHETICAL: NO (iv) ANTI-SENSE: NO (vi) ORIGINAL SOURCE:
    (A) ORGANISM: Neocallimastix patriciarum
    (B) STRAIN: 27

(vii) IMMEDIATE SOURCE:
    (A) LIBRARY: genomic DNA library
    (B) CLONE: pNspX-06

(ix) FEATURE:
    (A) NAME/KEY: CDS
    (B) LOCATION: 301..1755

(xi) SEQUENCE DESCRIPTION: SEQ ID NO:1:

```
ATATTATAAT AATTGTTCAA AAAAAGTAAT AATAAAAAAA AAATTTTTTT TTTTTTTTTT      60

GGGAAAATTG AGTATAAATA GTTTTTGGTT TACCTTTTTT GGTTTTTCCT TTATTCTTTA     120

TAAAGTTAAT TGTTTAATAA TTATTGGTGG AAATATTTAA AAGTTGTATA TATATTTTAA     180

TATTTATTGG AATTATTTAC TTTCACTGGT GGAAACAAAT ATTAATAGTG TATAATATAT     240

TATTAGAAAA AGAAAAAAAA AAATTATTAC AATTAATTAC TATAAATAAA ATAGTTAAAA     300

ATG AAA TTT TTA CAA ATT ATT CCT GTA TTA TTA TCT TTA ACT TCA ACT       348
Met Lys Phe Leu Gln Ile Ile Pro Val Leu Leu Ser Leu Thr Ser Thr
  1               5                  10                  15

ACT CTT GCT CAA AGT TTC TGT AGT TCA GCT TCT CAC TCT GGA CAA AGT       396
Thr Leu Ala Gln Ser Phe Cys Ser Ser Ala Ser His Ser Gly Gln Ser
             20                  25                  30

GTA AAG GAA ACC GGC AAC AAG GTT GGA ACT ATT GGT GGT GTT GGT TAC       444
Val Lys Glu Thr Gly Asn Lys Val Gly Thr Ile Gly Gly Val Gly Tyr
         35                  40                  45

GAA TTA TGG GCT GAT AGT GGT AAT AAC AGT GCT ACT TTC TAT TCT GAT       492
Glu Leu Trp Ala Asp Ser Gly Asn Asn Ser Ala Thr Phe Tyr Ser Asp
     50                  55                  60

GGT TCC TTC TCA TGT ACT TTC CAA AAT GCT GGG GAT TAC TTA TGT CGT       540
Gly Ser Phe Ser Cys Thr Phe Gln Asn Ala Gly Asp Tyr Leu Cys Arg
 65                  70                  75                  80

AGT GGT CTT TCT TTC GAT AGT ACT AAG ACC CCA TCT CAA ATT GGT CGT       588
Ser Gly Leu Ser Phe Asp Ser Thr Lys Thr Pro Ser Gln Ile Gly Arg
                 85                  90                  95

ATG AAG GCT GAT TTC AAA CTT GTC AAA ACA AAA TAT TTC CAA TGT TGG       636
Met Lys Ala Asp Phe Lys Leu Val Lys Thr Lys Tyr Phe Gln Cys Trp
            100                 105                 110

TTA TTC CTA TGT TGG TGT TTA CGG TGG ACT AGA AGT CCA CTT GTC GGA       684
Leu Phe Leu Cys Trp Cys Leu Arg Trp Thr Arg Ser Pro Leu Val Gly
        115                 120                 125

ATA CTA CAT GTC GAT AAT TGG CTT AGT CCA TCC CCA GGT GAT TGG           732
Ile Leu His Val Asp Asn Trp Leu Ser Pro Ser Pro Gly Asp Trp
    130                 135                 140

GTT GGT AAC AAG AAG CAT GGT TCT TTC ACT ATT GAT GGT GCT CAA TAC       780
Val Gly Asn Lys Lys His Gly Ser Phe Thr Ile Asp Gly Ala Gln Tyr
145                 150                 155                 160

ACT GTT TAT GAA AAC ACT CGT ACT GGT CCA TCT ATT GAT GGT AAT ACC       828
Thr Val Tyr Glu Asn Thr Arg Thr Gly Pro Ser Ile Asp Gly Asn Thr
                165                 170                 175

ACC TTC AAA CAA TAC TTT AGT ATT CGT CAA CAA GCT CGT GAT TGT GGT       876
Thr Phe Lys Gln Tyr Phe Ser Ile Arg Gln Gln Ala Arg Asp Cys Gly
            180                 185                 190

ACC ATT GAT ATT TCT GCT CAC TTT GAT CAA TGG GAA AAG CTT GGT ATG       924
```

-continued

```
Thr Ile Asp Ile Ser Ala His Phe Asp Gln Trp Glu Lys Leu Gly Met
            195                 200                 205

ACT ATG GGT AAA TTA CAT GAA GCC AAG GTT TTA GGT GAA GCC GGT AAC        972
Thr Met Gly Lys Leu His Glu Ala Lys Val Leu Gly Glu Ala Gly Asn
        210                 215                 220

GGT AAC GGT GGT GTC AGT GGT ACT GCT GAT TTC CCA TAC GCA AAG GTT       1020
Gly Asn Gly Gly Val Ser Gly Thr Ala Asp Phe Pro Tyr Ala Lys Val
225                 230                 235                 240

TAC ATT GGT GAT GGA AAT GGT GGT GGT GCT TCT CCA GCT CCA GCT GGT       1068
Tyr Ile Gly Asp Gly Asn Gly Gly Gly Ala Ser Pro Ala Pro Ala Gly
                245                 250                 255

GGC GCT CCA GCA GGC GGC GCT CCA GCC GGT AAC GAC CAA CCA CAA GGA       1116
Gly Ala Pro Ala Gly Gly Ala Pro Ala Gly Asn Asp Gln Pro Gln Gly
            260                 265                 270

CCA CAA GGT CAA CAA CCA CCA CAA GGT CAA CAA CCA CCA CAA GGT CAA       1164
Pro Gln Gly Gln Gln Pro Pro Gln Gly Gln Gln Pro Pro Gln Gly Gln
        275                 280                 285

CAA CCT CCA CAA GGC CAA CAA CCA CCA CAA GGC CAA CAA CCA CCA CAA       1212
Gln Pro Pro Gln Gly Gln Gln Pro Pro Gln Gly Gln Gln Pro Pro Gln
    290                 295                 300

GGT AAC GAT CAA CAA GGA CAA CAA CCA CCA CAA GGC CAA CAA CCA CCA       1260
Gly Asn Asp Gln Gln Gly Gln Gln Pro Pro Gln Gly Gln Gln Pro Pro
305                 310                 315                 320

CAA GGT AAC GAT CAA CAA CAA GGA CAA CAA CCA CCA CAA CCA CAA GGA       1308
Gln Gly Asn Asp Gln Gln Gln Gly Gln Gln Pro Pro Gln Pro Gln Gly
                325                 330                 335

CCA CAA GGA GGT AAC CCA GGT GGT TCT GAT TTT AAC AAC TGG AAC CAA       1356
Pro Gln Gly Gly Asn Pro Gly Gly Ser Asp Phe Asn Asn Trp Asn Gln
            340                 345                 350

GGT GGT AGT CCA TGG GGT GGT AAT CAA GGT GGT AGT CCA TGG GGA GGT       1404
Gly Gly Ser Pro Trp Gly Gly Asn Gln Gly Gly Ser Pro Trp Gly Gly
        355                 360                 365

AAC CAA GGC GGT AAT CCA TGG GGA GGA AAC CAA GGT GGT AGC CCA TGG       1452
Asn Gln Gly Gly Asn Pro Trp Gly Gly Asn Gln Gly Gly Ser Pro Trp
    370                 375                 380

GGT GGT AAC CAA GGT GGC AGT CCA TGG GGT CAA GGT AAC CAA GGC GGT       1500
Gly Gly Asn Gln Gly Gly Ser Pro Trp Gly Gln Gly Asn Gln Gly Gly
385                 390                 395                 400

AAT CCA TGG GGA GGA AAC CAA GGT GGT AGC CCA TGG GGT GGT AAC CAA       1548
Asn Pro Trp Gly Gly Asn Gln Gly Gly Ser Pro Trp Gly Gly Asn Gln
                405                 410                 415

GGT GGT AAT CCA TGG GGT GGT AAT CAA TGG GGT GCT CCA CAA AAT GCT       1596
Gly Gly Asn Pro Trp Gly Gly Asn Gln Trp Gly Ala Pro Gln Asn Ala
            420                 425                 430

GCT GCT CCA CAA AGC GCT GCT GCT CCA CAA AAC GCT TCT GAT GGT GGT       1644
Ala Ala Pro Gln Ser Ala Ala Ala Pro Gln Asn Ala Ser Asp Gly Gly
        435                 440                 445

AAC TGT GCT TCT CTT TGG GGT CAA TGC GGT GGA CAA GGT TAT AAT GGT       1692
Asn Cys Ala Ser Leu Trp Gly Gln Cys Gly Gly Gln Gly Tyr Asn Gly
    450                 455                 460

CCA TCT TGC TGT TCC GAA GGT TCC TGT AAG CCA ATT AAC GAA TAC TTC       1740
Pro Ser Cys Cys Ser Glu Gly Ser Cys Lys Pro Ile Asn Glu Tyr Phe
465                 470                 475                 480

CAC CAA TGT CAA AAA TAAATTGATT AGAAATCATT ATCAACCCAT ATTTATTTTG       1795
His Gln Cys Gln Lys
                485

TAGATTAAAA TAATAAAGAA AAAAAAAAAA ATTTTTTTTA TTTTTTTTTT TTTTTCTCCT    1855

CAATTAATAA ATCATTAAAA TAGATCATTA ATATAATTAT TTATTTTCAT TTTTTTTTTT    1915
```

```
                                   -continued

TTTAATTAAT ACGTAAATGT AAATGTAAAT TTAAACAATT TATTTAATAT TTAATATTTT      1975

ATAAAAGATA CTATTTTAAT AAAATTATAA AAAAAAAATA TATAAAAAAA AAATATAAAA      2035

AAAAAAAAAA TATTAATGAA AGT                                             2058

(2) INFORMATION FOR SEQ ID NO:2:

(i) SEQUENCE CHARACTERISTICS:
         (A) LENGTH: 485 amino acids
         (B) TYPE: amino acid
         (D) TOPOLOGY: linear (ii) MOLECULE TYPE: protein (xi) SEQUENCE DESCRIPTION: SEQ ID NO:2:

Met Lys Phe Leu Gln Ile Ile Pro Val Leu Leu Ser Leu Thr Ser Thr
 1               5                  10                  15

Thr Leu Ala Gln Ser Phe Cys Ser Ser Ala Ser His Ser Gly Gln Ser
            20                  25                  30

Val Lys Glu Thr Gly Asn Lys Val Gly Thr Ile Gly Gly Val Gly Tyr
        35                  40                  45

Glu Leu Trp Ala Asp Ser Gly Asn Asn Ser Ala Thr Phe Tyr Ser Asp
    50                  55                  60

Gly Ser Phe Ser Cys Thr Phe Gln Asn Ala Gly Asp Tyr Leu Cys Arg
65                  70                  75                  80

Ser Gly Leu Ser Phe Asp Ser Thr Lys Thr Pro Ser Gln Ile Gly Arg
                85                  90                  95

Met Lys Ala Asp Phe Lys Leu Val Lys Thr Lys Tyr Phe Gln Cys Trp
            100                 105                 110

Leu Phe Leu Cys Trp Cys Leu Arg Trp Thr Arg Ser Pro Leu Val Gly
        115                 120                 125

Ile Leu His Val Asp Asn Trp Leu Ser Pro Ser Pro Gly Asp Trp
    130                 135                 140

Val Gly Asn Lys Lys His Gly Ser Phe Thr Ile Asp Gly Ala Gln Tyr
145                 150                 155                 160

Thr Val Tyr Glu Asn Thr Arg Thr Gly Pro Ser Ile Asp Gly Asn Thr
                165                 170                 175

Thr Phe Lys Gln Tyr Phe Ser Ile Arg Gln Gln Ala Arg Asp Cys Gly
            180                 185                 190

Thr Ile Asp Ile Ser Ala His Phe Asp Gln Trp Glu Lys Leu Gly Met
        195                 200                 205

Thr Met Gly Lys Leu His Glu Ala Lys Val Leu Gly Glu Ala Gly Asn
    210                 215                 220

Gly Asn Gly Gly Val Ser Gly Thr Ala Asp Phe Pro Tyr Ala Lys Val
225                 230                 235                 240

Tyr Ile Gly Asp Gly Asn Gly Gly Ala Ser Pro Ala Pro Ala Gly
                245                 250                 255

Gly Ala Pro Ala Gly Gly Ala Pro Ala Gly Asn Asp Gln Pro Gln Gly
            260                 265                 270

Pro Gln Gly Gln Gln Pro Pro Gln Gly Gln Gln Pro Pro Gln Gly Gln
        275                 280                 285

Gln Pro Pro Gln Gly Gln Gln Pro Pro Gln Gly Gln Gln Pro Pro Gln
    290                 295                 300

Gly Asn Asp Gln Gln Gly Gln Gln Pro Pro Gln Pro Gln Pro Gln Gly
305                 310                 315                 320

Gln Gly Asn Asp Gln Gln Gln Gly Gln Gln Pro Pro Gln Pro Gln Gly
```

```
                    325                 330                 335
Pro Gln Gly Gly Asn Pro Gly Ser Asp Phe Asn Asn Trp Asn Gln
                340                 345                 350
Gly Gly Ser Pro Trp Gly Gly Asn Gln Gly Gly Ser Pro Trp Gly Gly
            355                 360                 365
Asn Gln Gly Gly Asn Pro Trp Gly Gly Asn Gln Gly Gly Ser Pro Trp
370                 375                 380
Gly Gly Asn Gln Gly Gly Ser Pro Trp Gly Gly Asn Gln Gly Gly
385                 390                 395                 400
Asn Pro Trp Gly Gly Asn Gln Gly Gly Ser Pro Trp Gly Gly Asn Gln
                405                 410                 415
Gly Gly Asn Pro Trp Gly Gly Asn Gln Trp Gly Ala Pro Gln Asn Ala
                420                 425                 430
Ala Ala Pro Gln Ser Ala Ala Ala Pro Gln Asn Ala Ser Asp Gly Gly
                435                 440                 445
Asn Cys Ala Ser Leu Trp Gly Gln Cys Gly Gly Gln Gly Tyr Asn Gly
                450                 455                 460
Pro Ser Cys Cys Ser Glu Gly Ser Cys Lys Pro Ile Asn Glu Tyr Phe
465                 470                 475                 480
His Gln Cys Gln Lys
                485

(2) INFORMATION FOR SEQ ID NO:3:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide XI"

(iii) HYPOTHETICAL: NO (iv) ANTI-SENSE: NO (xi) SEQUENCE DESCRIPTION: SEQ ID NO:3:

ATCTCTAGAA TTCAACTACT CTTGCTCAAA G                              31

(2) INFORMATION FOR SEQ ID NO:4:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide XII"

(iii) HYPOTHETICAL: NO (iv) ANTI-SENSE: NO (xi) SEQUENCE DESCRIPTION: SEQ ID NO:4:

GGGTTGCTCG AGATTTCTAA TCAATTTAT                                 29

(2) INFORMATION FOR SEQ ID NO:5:

(i) SEQUENCE CHARACTERISTICS:
        (A) LENGTH: 32 base pairs
        (B) TYPE: nucleic acid
        (C) STRANDEDNESS: single
```

```
        (D) TOPOLOGY: linear (ii) MOLECULE TYPE: other nucleic acid
        (A) DESCRIPTION: /desc = "oligonucleotide XIII"

(iii) HYPOTHETICAL: NO (iv) ANTI-SENSE: NO (xi) SEQUENCE DESCRIPTION: SEQ ID NO:5:

GCGAATTCAT GTCAACTCTT GCTCAAAGTT TC                                            32

(2) INFORMATION FOR SEQ ID NO:6:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide XIV"

(iii) HYPOTHETICAL: NO (iv) ANTI-SENSE: NO (xi) SEQUENCE DESCRIPTION: SEQ ID NO:6:

GCCTGCAGTG ATTTCTAATC AATTTAT                                                  27
```